(12) United States Patent
Akimoto et al.

(10) Patent No.: US 7,659,912 B2
(45) Date of Patent: Feb. 9, 2010

(54) INSERTION SUPPORT SYSTEM FOR PRODUCING IMAGINARY ENDOSCOPIC IMAGE AND SUPPORTING INSERTION OF BRONCHOSCOPE

(75) Inventors: Shunya Akimoto, Kawasaki (JP); Junichi Ohnishi, Hachioji (JP)

(73) Assignee: Olympus Corporation, Tokyo (JP)

( * ) Notice: Subject to any disclaimer, the term of this patent is extended or adjusted under 35 U.S.C. 154(b) by 315 days.

(21) Appl. No.: 11/395,101

(22) Filed: Mar. 31, 2006

(65) Prior Publication Data

US 2006/0170765 A1 Aug. 3, 2006

Related U.S. Application Data

(63) Continuation of application No. PCT/JP2004/016035, filed on Oct. 28, 2004.

(30) Foreign Application Priority Data

Oct. 29, 2003 (JP) .............................. 2003-369556

(51) Int. Cl.
| | |
|---|---|
| *G09G 5/00* | (2006.01) |
| *G06T 17/00* | (2006.01) |
| *H04N 13/00* | (2006.01) |
| *A62B 1/04* | (2006.01) |
| *A61B 1/04* | (2006.01) |
| *H04N 7/00* | (2006.01) |
| *A61B 1/00* | (2006.01) |

(52) U.S. Cl. ...................... 345/619; 345/420; 345/629; 345/649; 348/45; 348/65; 348/77; 348/113; 600/117; 600/118

(58) Field of Classification Search ................. 345/619, 345/420, 629, 649; 348/45, 65, 77, 113
See application file for complete search history.

(56) References Cited

U.S. PATENT DOCUMENTS

| 5,704,897 | A | 1/1998 | Truppe ........................ 600/117 |
|---|---|---|---|
| 6,346,940 | B1* | 2/2002 | Fukunaga .................... 345/420 |
| 2002/0007108 | A1 | 1/2002 | Chen et al. ................... 600/117 |
| 2005/0027167 | A1* | 2/2005 | Chatenever et al. .......... 600/173 |
| 2005/0122343 | A1* | 6/2005 | Bailey et al. ................. 345/619 |
| 2007/0046661 | A1* | 3/2007 | Ma et al. ..................... 345/419 |
| 2007/0173694 | A1* | 7/2007 | Tsuji et al. ................... 600/146 |
| 2008/0117230 | A1* | 5/2008 | Wegenkittl et al. ........... 345/619 |

FOREIGN PATENT DOCUMENTS

| JP | 2000-135215 | 5/2000 |
|---|---|---|
| JP | 2002-200030 | 7/2002 |
| JP | 2002-306403 | 10/2002 |
| JP | 2002-345725 | 12/2002 |

OTHER PUBLICATIONS

Wagner, Daniel, "EndoView: a System for Fast Virtual Endoscopic Rendering and Registration", 2001, p. 1-84.*

* cited by examiner

*Primary Examiner*—Ryan R Yang
(74) *Attorney, Agent, or Firm*—Scully, Scott, Murphy & Presser, P.C.

(57) ABSTRACT

In an insertion support system according to the present invention, on the basis of the rotation angle data of the VBS images stored in the memory, an image processing unit rotates and corrects the VBS image and the thumbnail VBS images to generate the insertion support screen.

4 Claims, 30 Drawing Sheets

FIG.14

ROTATION ANGLE CANNOT BE SET AT 180° OR MORE.

PLEASE RETRY SETTING.

INSERTION SUPPORT SYSTEM FOR PRODUCING IMAGINARY ENDOSCOPIC IMAGE AND SUPPORTING INSERTION OF BRONCHOSCOPE

CROSS REFERENCE TO RELATED APPLICATION

This application is a continuation application of PCT/JP2004/016035 filed on Oct. 28, 2004 and claims benefit of Japanese Application No. 2003-369556 filed in Japan on Oct. 29, 2003, the entire contents of which are incorporated herein by this reference.

BACKGROUND OF THE INVENTION

1. Field of the Invention

The present invention relates to an insertion support system for supporting insertion of an endoscope.

2. Description of the Related Art

In recent years, diagnosis using an image has been widely performed. For example, a cross-sectional image of a subject is captured by using an X-ray CT (Computed Tomography) apparatus or the like to obtain three-dimensional image data of the subject. The obtained three-dimensional image data is then used for diagnosing an affected area.

The CT apparatus continuously performs X-ray irradiation and detection in a direction of the body axis of the subject while continuously rotating the subject. Thereby, spiral and continuous scanning (i.e., helical scanning) is performed for a three-dimensional region in the subject, and a three-dimensional image is produced from successive cross-sectional slice images of the three-dimensional region.

Such three-dimensional images include a three-dimensional image of the bronchi of the lungs. The three-dimensional image of the bronchi is used for three-dimensionally locating the position of an abnormal area suspected to contain lung cancer, for example. Then, to examine the abnormal area through a biopsy, a bronchoscope is inserted and a tissue sample is obtained by using a biopsy needle, biopsy forceps, or the like which is protruded from a distal end of the bronchoscope.

In a duct within the body that branches in multiple stages, such as the bronchi, if the abnormal area is located near a periphery of a branch, it is difficult to make the distal end of the endoscope correctly reach a target location within a short time period. Therefore, Japanese Unexamined Patent Application Publication No. 2000-135215, for example, proposes an apparatus which navigates the bronchoscope to the target location by producing a three-dimensional image of the duct within the subject on the basis of image data of the three-dimensional region in the subject, determining a route leading to a target point along the duct on the three-dimensional image, producing a virtual endoscope image of the duct along the route based on the image data, and then displaying the virtual endoscope image.

SUMMARY OF THE INVENTION

An insertion support system according to the present invention includes: virtual image generating means for generating three-dimensional images of a duct in a body cavity in a subject as successive virtual images in frame units on the basis of image data of a three-dimensional region in the subject; navigation image generating means for generating a navigation image including an endoscope image sent by an endoscope configured to capture images of the duct in the body cavity in the subject, the virtual image, and a plurality of reduced size images of the virtual image at all branch points at which the duct in the body cavity in the subject diverges; rotation information storing means for storing image rotation information of the reduced size images; and image rotation controlling means for rotating the reduced size images generated by the navigation image generating means, on the basis of the image rotation information.

BRIEF DESCRIPTION OF THE DRAWINGS

FIG. 14 is a diagram showing an error display window appearing in the processing of FIG. 10.

DETAILED DESCRIPTION OF THE PREFERRED EMBODIMENT(S)

With reference to the drawings, an embodiment of the present invention will now be described below.

Embodiment 1

Figure 1:
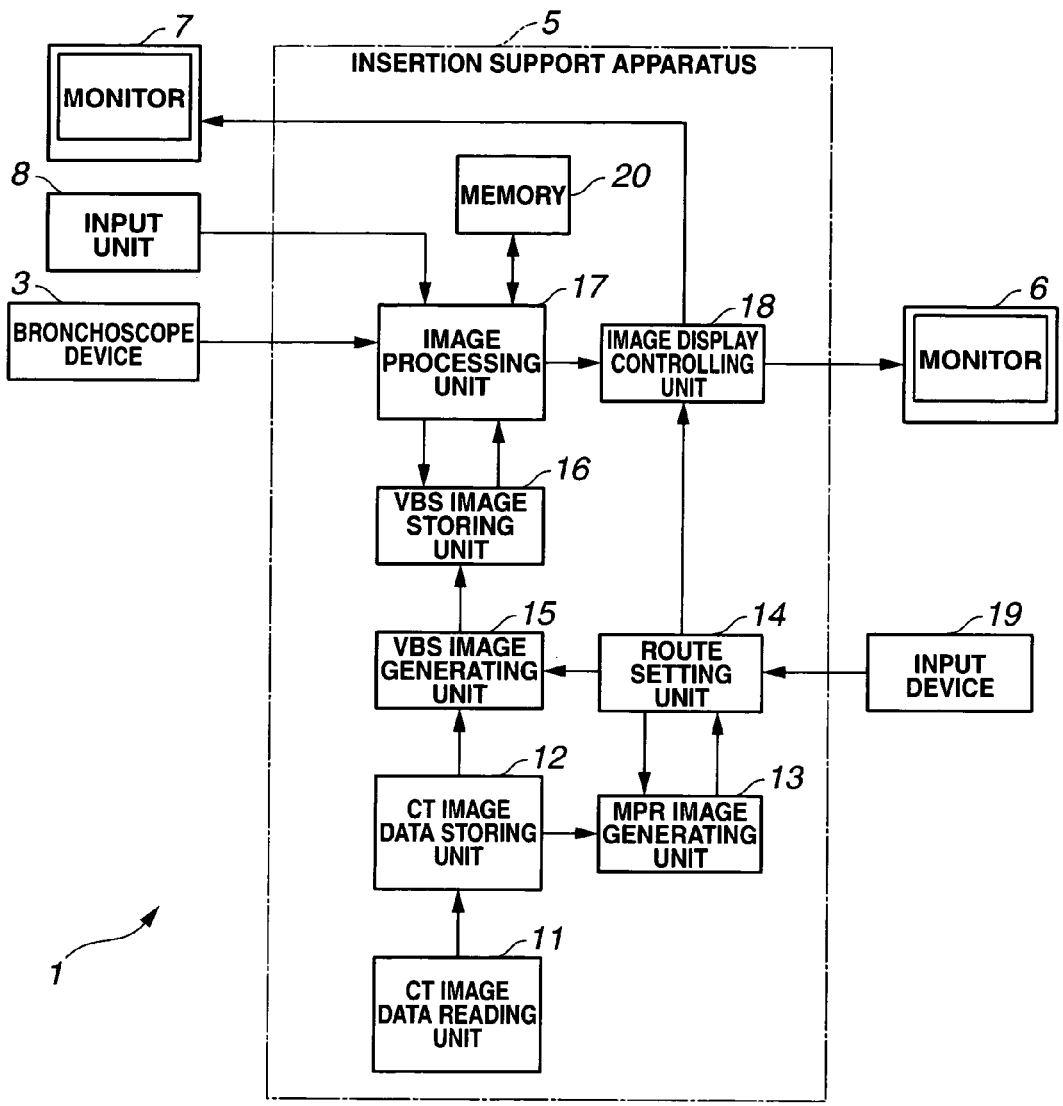
FIG. 1 is a configuration diagram illustrating a configuration of an insertion support system to support insertion into the bronchi according to a first embodiment of the present invention.

As illustrated in FIG. 1, a bronchi insertion support system 1 according to the present embodiment includes a bronchoscope device 3 and an insertion support apparatus 5.

The insertion support apparatus 5 supports insertion of the bronchoscope device 3 into the bronchi by generating a virtual endoscope image (hereinafter referred to as a VBS image) of the interior of the bronchi on the basis of CT image data, combining the VBS image with an endoscope image (hereinafter referred to as a live image) obtained by the bronchoscope device 3, and displaying a resultant image on a monitor 6.

The bronchoscope device 3 includes a bronchoscope having image pick-up means, a light source for supplying illuminating light to the bronchoscope, a camera controlling unit for performing signal processing on an image pickup signal sent by the bronchoscope, and the like, which are not illustrated in the figure. The bronchoscope device 3 inserts the bronchoscope into the bronchi of a patient, captures images of the interior of the bronchi, performs a biopsy to check tissue of an affected area located at a periphery of the bronchi, combines the live image with the VBS image, and displays a resultant image on a monitor 7.

The monitor 7 includes an input unit 8 having a pointing device, such as a touch screen, so that a user can easily operate the input unit 8 including the touch panel while performing an insertion procedure.

The insertion support apparatus 5 includes a CT image data reading unit 11 which reads CT image data, i.e., three-dimensional image data generated by a known CT apparatus (not illustrated) that captures X-ray cross-sectional images of a patient, through a portable data storage medium, such as an MO (Magnetic Optical) disk device, a DVD (Digital Versatile Disk) device, or the like, for example; and a CT data storing unit 12 which stores the CT image data read by the CT image data reading unit 11. The insertion support apparatus 5 further includes an MPR image generating unit 13 which generates an MPR image (a multi-planar reformatted image) on the basis of the CT image data stored in the CT image data storing unit 12, and a route setting unit 14 which generates a route setting screen (later described) including the MPR image generated by the MPR image generating unit 13 and which sets a support route (hereinafter simply referred to as a route) leading to the bronchi for supporting the bronchoscope device 3. The insertion support apparatus 5 further includes a VBS image generating unit 15 which serves as virtual image generating means for generating successive VBS images of the route set by the route setting unit 14 in frame units on the basis of the CT image data stored in the CT image data storing unit 12; and a VBS image storing unit 16 which stores the VBS images generated by the VBS image generating unit 15. The insertion support apparatus 5 further includes an image processing unit 17 which receives inputs of the image pickup signal sent by the bronchoscope device 3 and an input signal sent by the input unit 8 and which generates an insertion support screen (later described) including the live image, the VBS image, and a plurality of thumbnail VBS images; and an image display controlling unit 18 which displays, on the monitor 6, the route setting screen generated by the route setting unit 14 and the insertion support screen generated by the image processing unit 17. The insertion support apparatus 5 further includes an input device 19 which includes a keyboard and a pointing device for inputting set information in the route setting unit 14; and a memory 20 which stores rotation angle data of the VBS images based on the input signal sent by the input unit 8, with the rotation angle data being linked to frame information of the VBS images.

Figure 2:
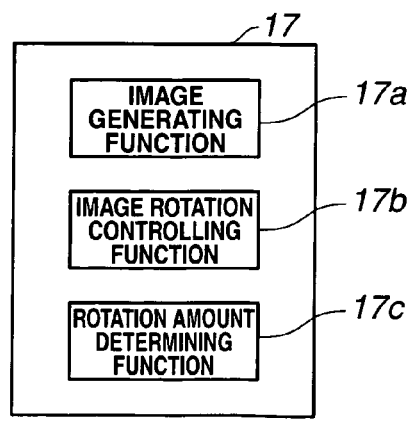
FIG. 2 is a block diagram illustrating a functional configuration of the image processing unit of FIG. 1.

As illustrated in FIG. 2, the image processing unit 17 includes an image generating function 17a which serves as navigation image generating means, an image rotation controlling function 17b which serves as image rotation controlling means, and a rotation amount determining function 17c which serves as rotation amount comparing means. In the image processing unit 17, on the basis of the rotation angle data of one of the VBS images stored in the memory 20, the image rotation controlling function 17b performs control to rotate and correct the VBS image and the thumbnail VBS images, and the image generating function 17a generates the insertion support screen. Further, the rotation amount determining function 17c determines the rotation angle data.

On the basis of a result of the determination of the rotation angle data made by the rotation amount determining function 17c, the image rotation controlling function 17b performs rotation control of the VBS image and the thumbnail VBS images. The rotation control will be later described in detail.

The bronchoscope device 3 receives the VBS image and the thumbnail VBS images from the image processing unit 17 of the insertion support apparatus 5, combines the received VBS image and thumbnail VBS images with the live image, and displays, on the monitor 7, a screen similar to the insertion support screen displayed on the monitor 6 by the insertion support apparatus 5. Further, the bronchoscope device 3 outputs input information sent by the input unit 8 which includes the touch sensor of the monitor 7, to the image processing unit 17 of the insertion support apparatus 5.

The CT image data storing unit 12 and the VBS image storing unit 16 may be formed by one hard disk. Further, the MPR image generating unit 13, the route setting unit 14, the VBS image generating unit 15, and the image processing unit 17 may be formed by one arithmetic processing circuit. The CT image data reading unit 11 described above reads the CT image data through the portable data storage medium, such as the MO, the DVD, or the like. If a CT apparatus or an in-house server which stores the CT image data is connected to an in-house LAN, the CT image data reading unit 11 may be formed by an interface circuit connectable to the in-house LAN so that the CT image data is read through the in-house LAN.

Operations according to the thus configured present embodiment will now be described.

Figure 3:
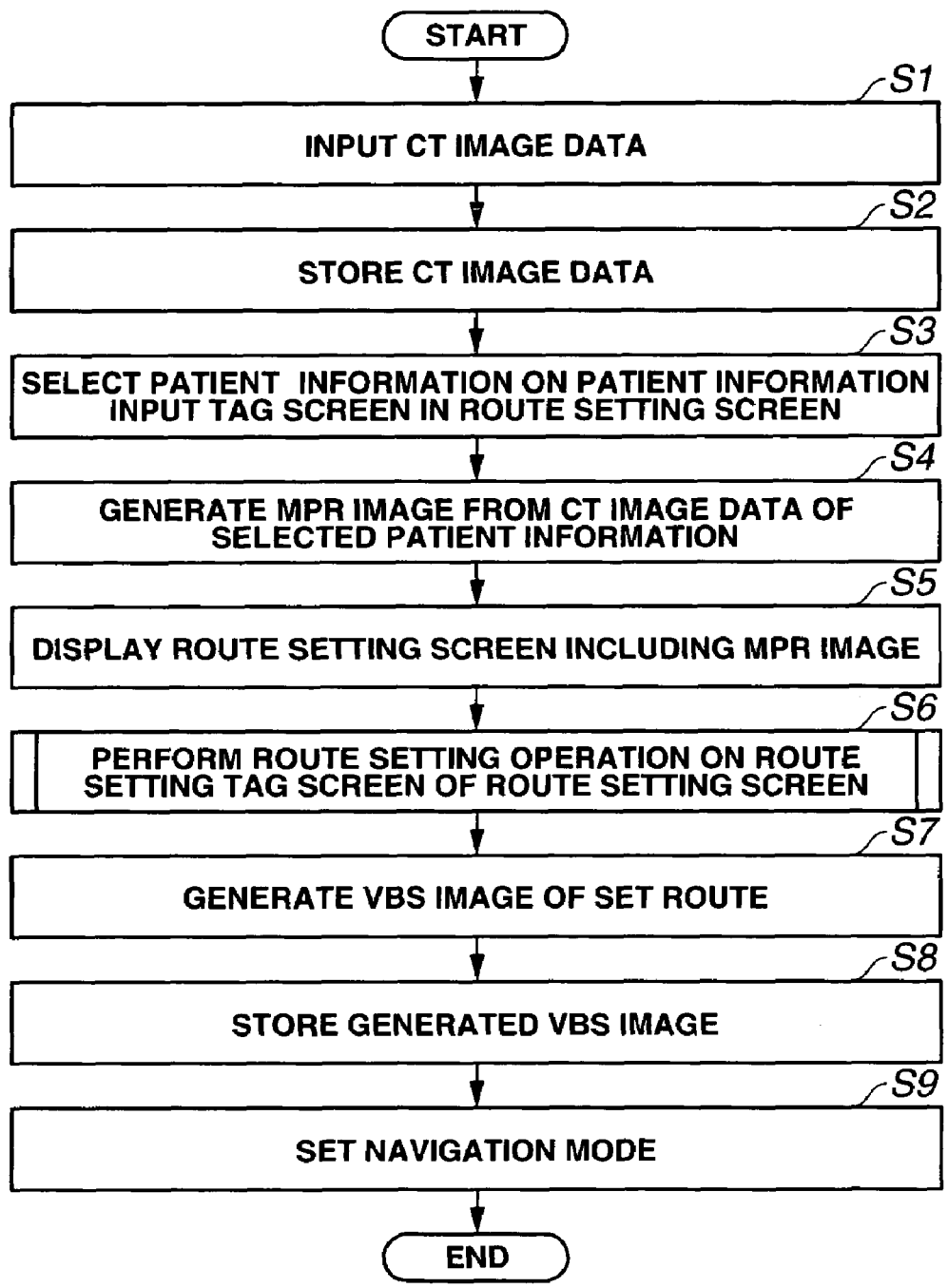
FIG. 3 is a flowchart illustrating a flow of a navigation data generating processing, which is a first preparation for insertion support performed by the insertion support apparatus of FIG. 1.

As illustrated in FIG. 3, prior to observation and treatment using the bronchoscope device 3, in the insertion support apparatus 5, the CT image data reading unit 11 reads the CT image data of the patient generated by the CT apparatus at Step S1. The thus read CT image data is stored in the CT image data storing unit 12 at Step S2.

Figure 4:
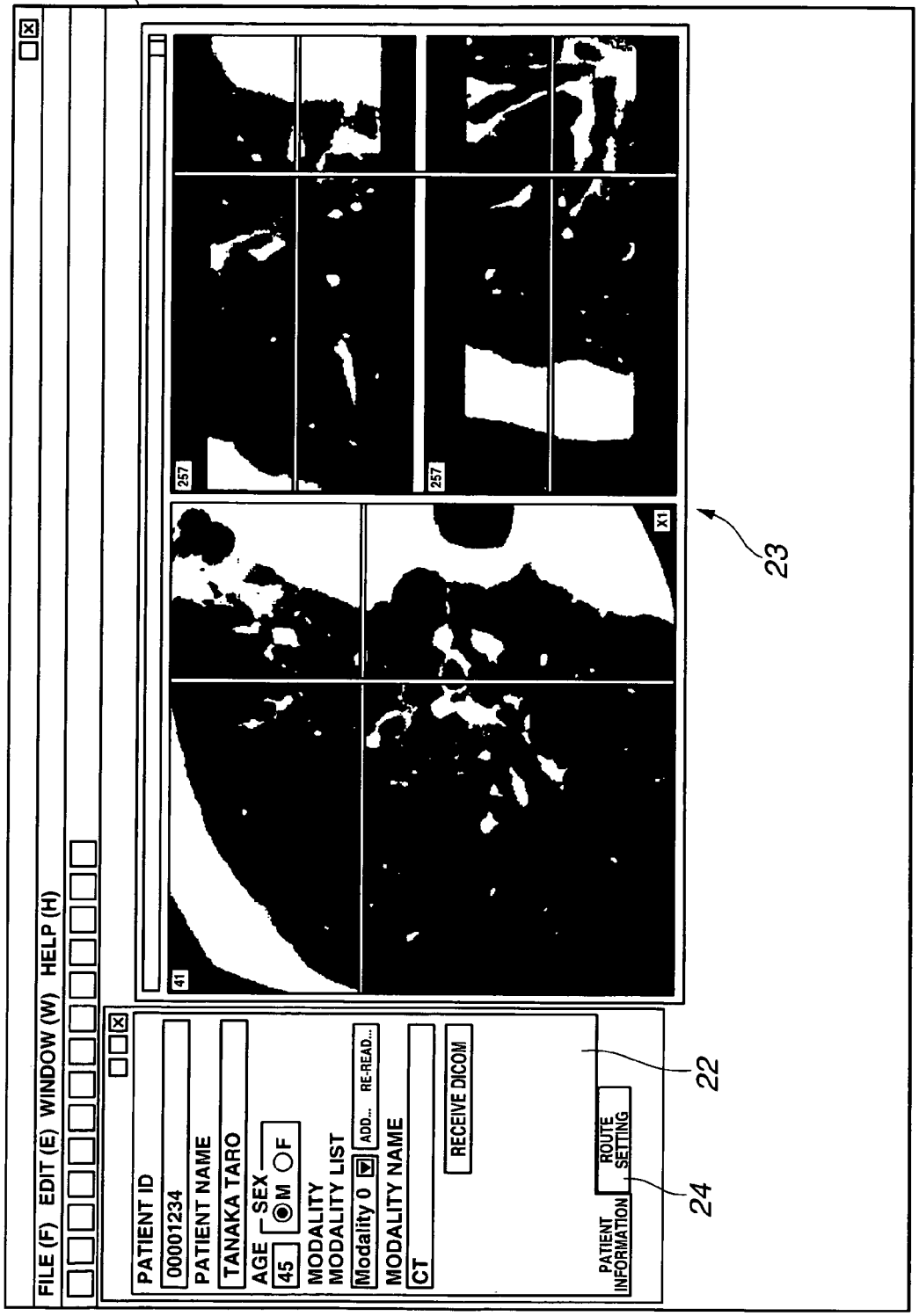
FIG. 4 is a first diagram showing the route setting screen appearing in the processing of FIG. 3.

At Step S3, the route setting unit 14 displays a route setting screen 21 as shown in FIG. 4 on the monitor 6, and patient information shown in a patient information tag screen 22 on the route setting screen 21 is selected. Upon this selection, an MPR image 23 including, for example, three different multi-planar images of the selected patient is generated at Step S4. The thus generated MPR image 23 is displayed on the route setting screen 21 at Step S5.

The selection of the patient information on the patient information tag screen 22 is made by inputting a patient ID which identifies one of the patients using the input device 19.

Figure 5:
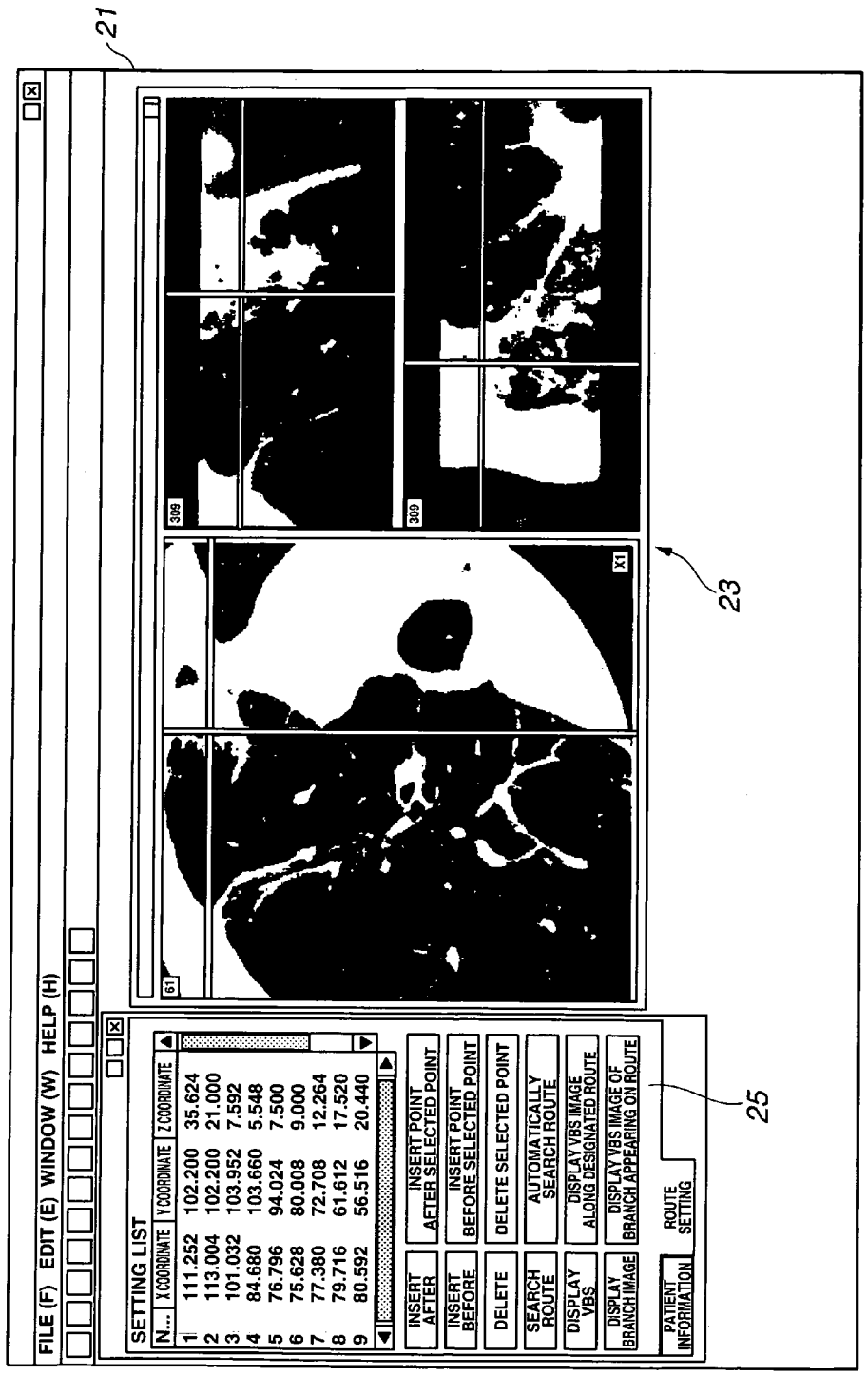
FIG. 5 is a second diagram showing the route setting screen appearing in the processing of FIG. 3.

Then, at Step S6, a route setting tag 24 (refer to FIG. 4) on the route setting screen 21 is selected using the input device 19. Thereby, a route setting tag screen 25 as shown in FIG. 5 is displayed on the route setting screen 21, and a route setting processing (later described) is performed to set a route in the bronchi for supporting insertion of the bronchoscope.

When the route for supporting the insertion has been set, successive VBS images of the entirety of the set route are generated in frame units by the VBS image generating unit 15 at Step S7. The generated VBS images are stored in the VBS image storing unit 16 at Step S8.

As the above processings of Steps S1 to S8 are performed, the first preparation for the insertion support, which is performed by the insertion support apparatus 5 in the observation and treatment using the bronchoscope, is completed.

Figure 6:
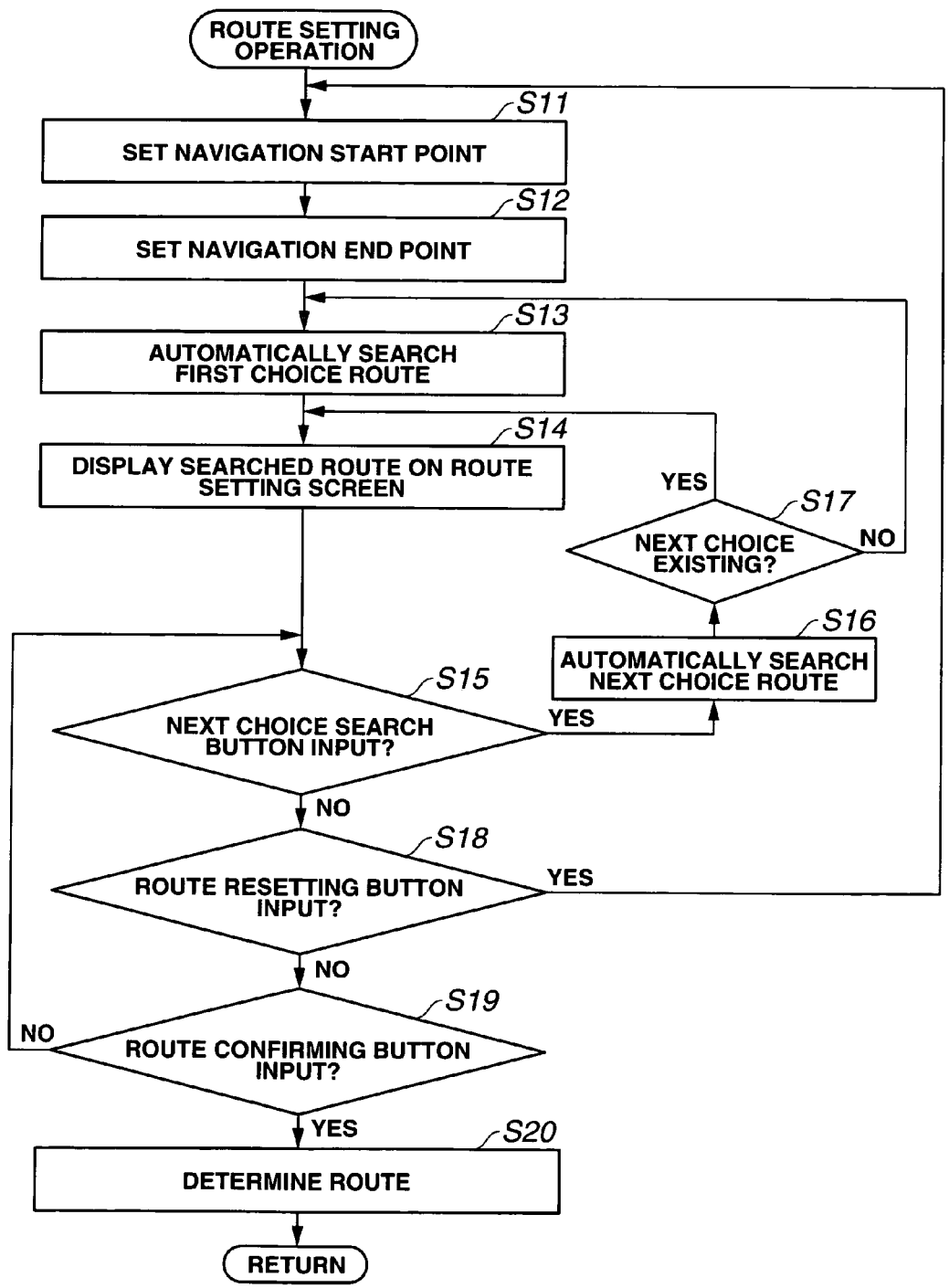
FIG. 6 is a flowchart illustrating a flow of the route setting processing of FIG. 3.

With reference to FIG. 6, the route setting processing performed at Step S6 will now be described.

Figure 7:
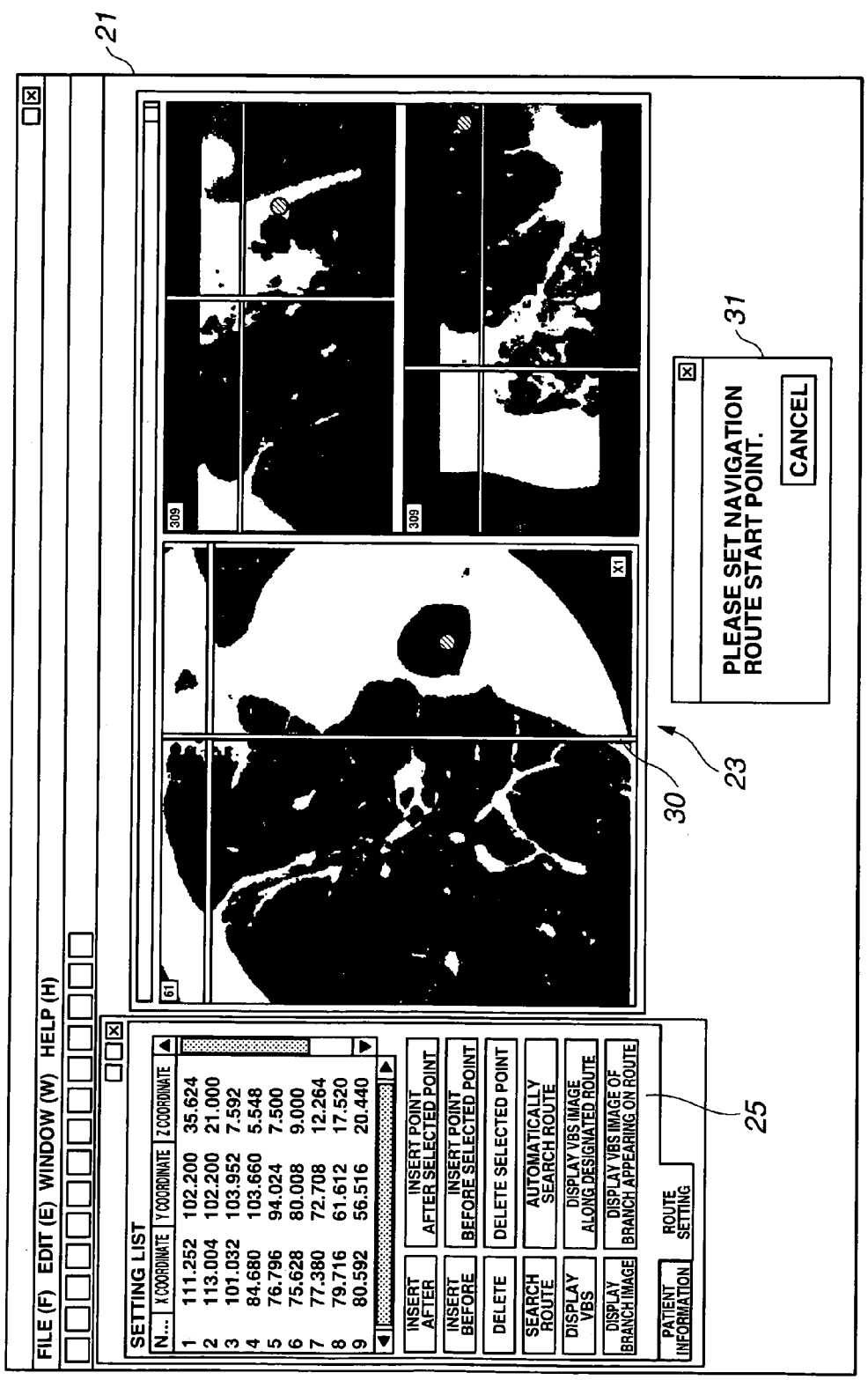
FIG. 7 is a first diagram showing the route setting screen appearing in the processing of FIG. 6.
Figure 8:
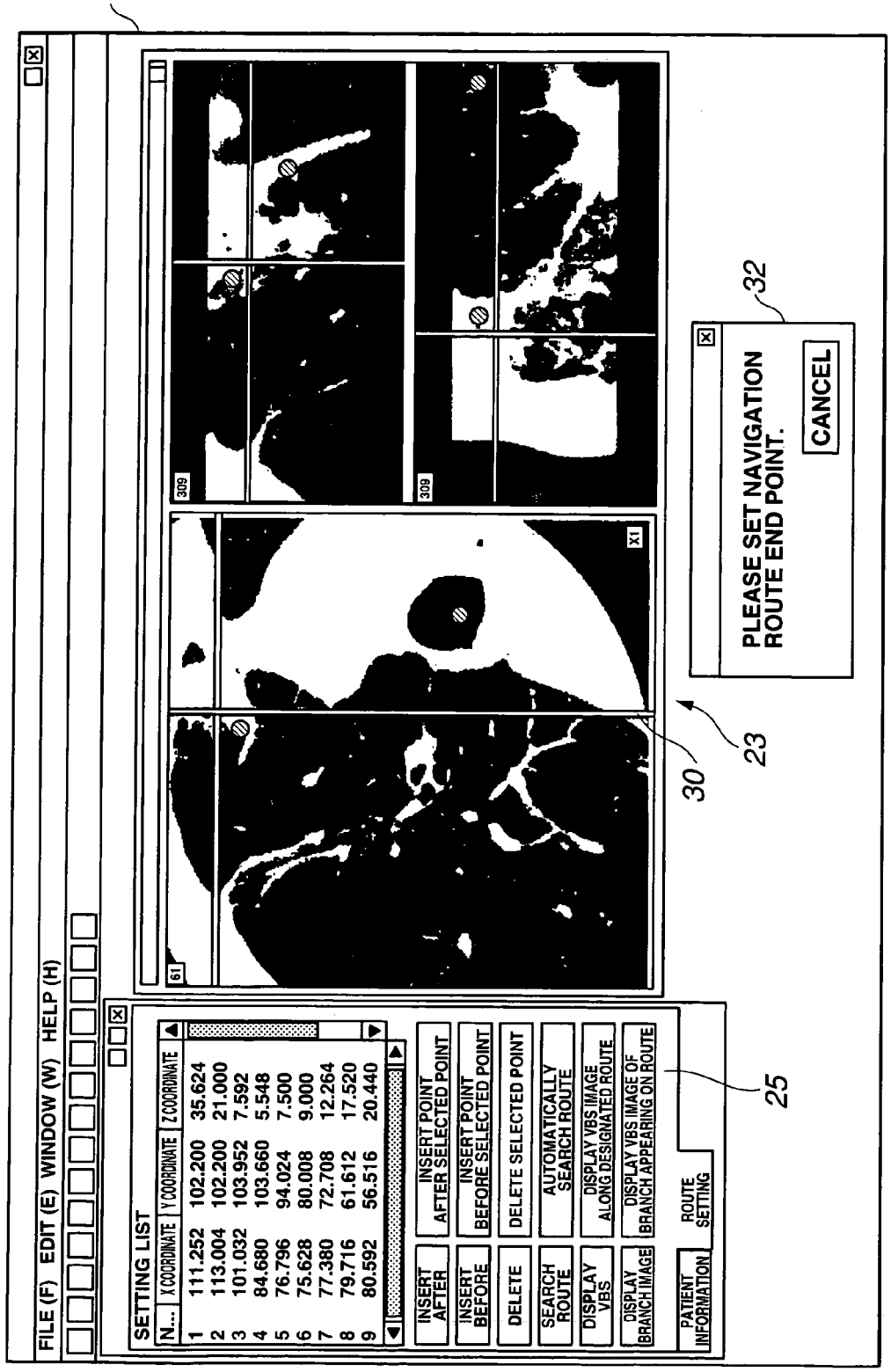
FIG. 8 is a second diagram showing the route setting screen appearing in the processing of FIG. 6.

As illustrated in FIG. 6, in the route setting processing performed at Step S6, the input device 19 is operated to click a route search button on the route setting tag screen 25 shown in FIG. 5. Thereby, at Step S11, a start point input command window 31 as shown in FIG. 7 which prompts input of a route start point is displayed on the route setting screen 21. Then, the start point is set on one of the cross-sectional images forming the MPR image 23 by using a cursor 30 on the route setting screen 21. Upon setting of the start point, the start point is also set at a corresponding position in each of the other two cross-sectional images forming the MPR image 23. Further, an end point input command window 32 as shown in FIG. 8 which prompts input of a route end point is displayed on the route setting screen 21.

Then, in a similar manner to the setting of the start point, the end point is set on one of the cross-sectional images forming the MPR image 23 by using the cursor 30 on the route setting screen 21 at Step S12. Upon setting of the end point, the end point is also set at a corresponding position in each of the other two cross-sectional images forming the MPR image 23.

When the start point and the end point have been set, the route setting unit 14 searches a route in the bronchi connecting the start point and the end point at Step S13. The bronchi have complicated pathways. Therefore, the route in the bronchi connecting the start point and the end point is not necessarily determined uniquely. In view of this, the route setting unit 14 searches a first choice of the route in the bronchi connecting the start point and the end point at Step S13.

Figure 9:
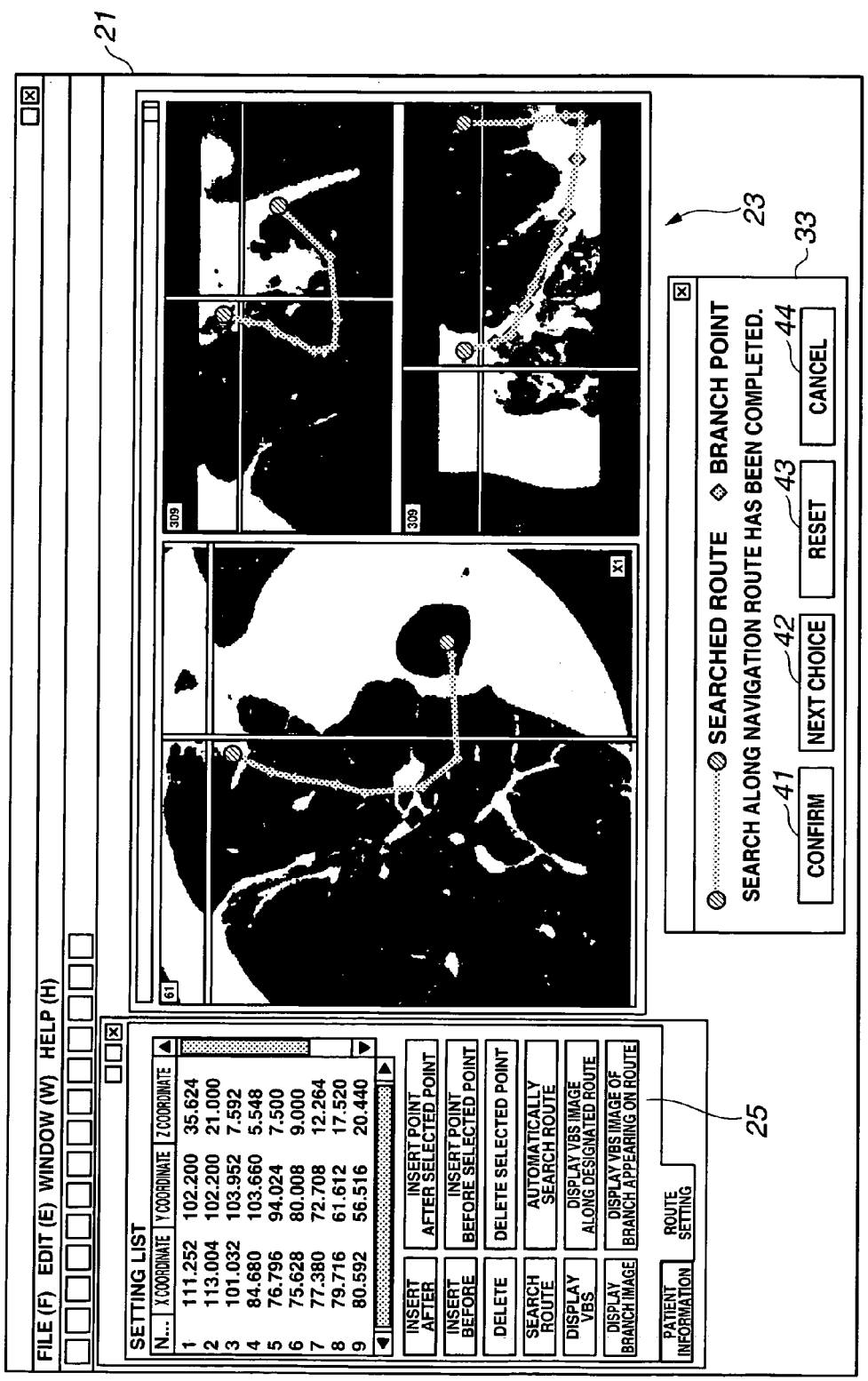
FIG. 9 is a third diagram showing the route setting screen appearing in the processing of FIG. 6.

Then, at Step S14, as illustrated in FIG. 9, on the route setting screen 21, the route setting unit 14 displays the searched route superimposed on the MPR image 23, and also displays a route confirmation window 33 which prompts an input indicating confirmation of the searched route, or the like.

The route confirmation window 33 includes a route confirmation button 41 for commanding confirmation of the searched route, a next choice search button 42 for commanding search of a next choice route, a route reset button 43 for setting again the start point and the end point, and a cancel button 44 for canceling a route search processing.

At Step S15, it is determined whether the next choice search button 42 has been clicked. If it is determined that the next choice search button 42 has been clicked, the next choice route is automatically searched at Step S16, and the flow advances to Step S17. If it is determined that the next choice search button 42 has not been clicked, the flow advances to Step S18. At Step S17, on the basis of the result of the search for the next choice route, it is determined whether the next choice route exists. If it is determined that the next choice route does not exist, a warning message notifying nonexistence of the next choice route (not shown) is displayed, and the flow returns to Step S13. If it is determined that the next choice route exists, the flow returns to Step S14.

At Step S18, it is determined whether the route reset button 43 has been clicked. If it is determined that the route reset button 43 has been clicked, the flow returns to Step S11. If it is determined that the route reset button 43 has not been clicked, the flow advances to Step S19.

At Step S19, it is determined whether the route confirmation button 41 has been clicked. If it is determined that the route confirmation button 41 has not been clicked, the flow returns to Step S15. If it is determined that the route confirmation button 41 has been clicked, the flow advances to Step S20. At Step S20, the route and position information of each of the branch points on the route are determined, and the flow returns to Step S7 of FIG. 3.

Description will now be made of an insertion simulation, i.e., a second preparation for the insertion support performed prior to a bronchoscope observation procedure by the insertion support apparatus 5 which has set the route as described above. In the following example described below, the route has ten branch points.

Figure 10:
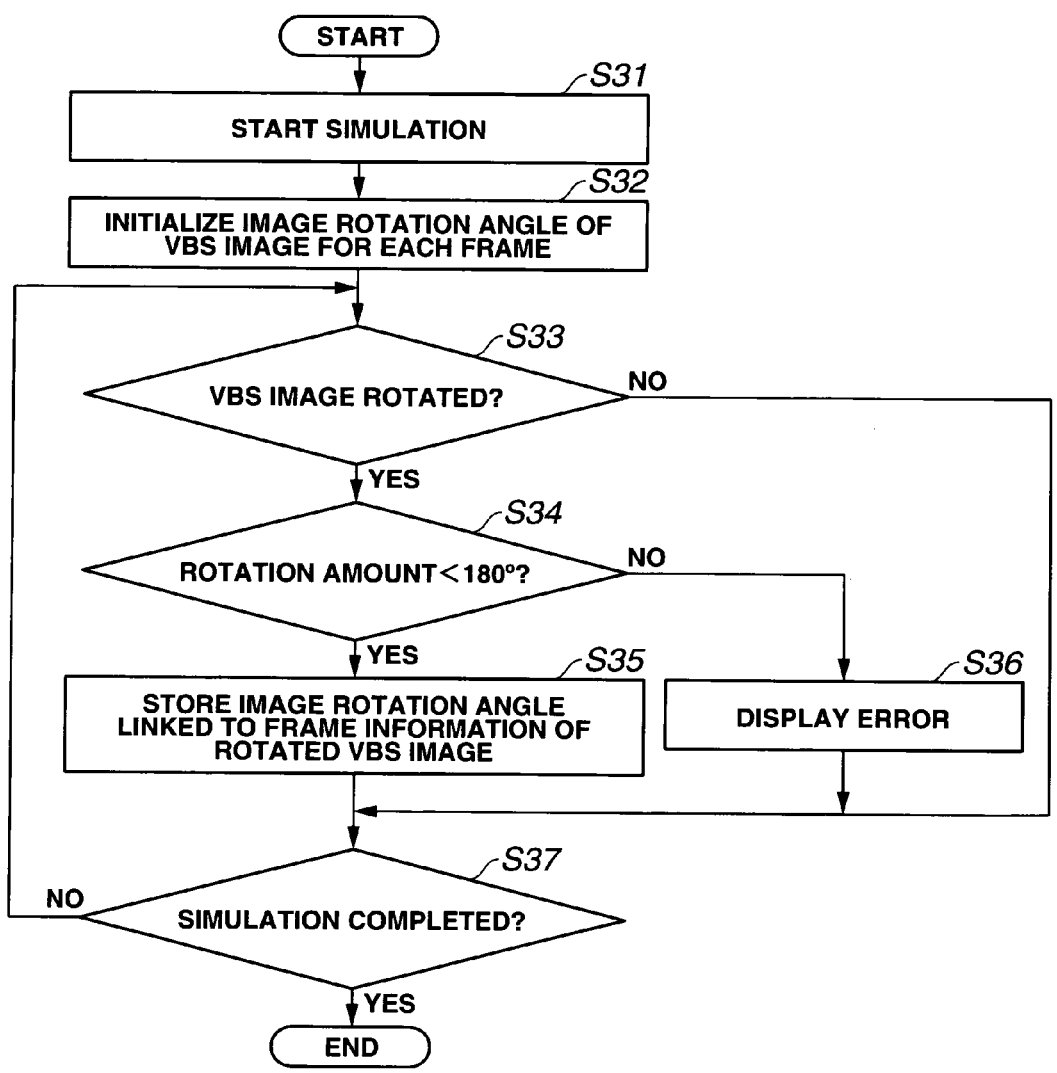
FIG. 10 is a flowchart illustrating a flow of a simulation processing, which is a second preparation for the insertion support performed by the insertion support apparatus of FIG. 1.
Figure 11:
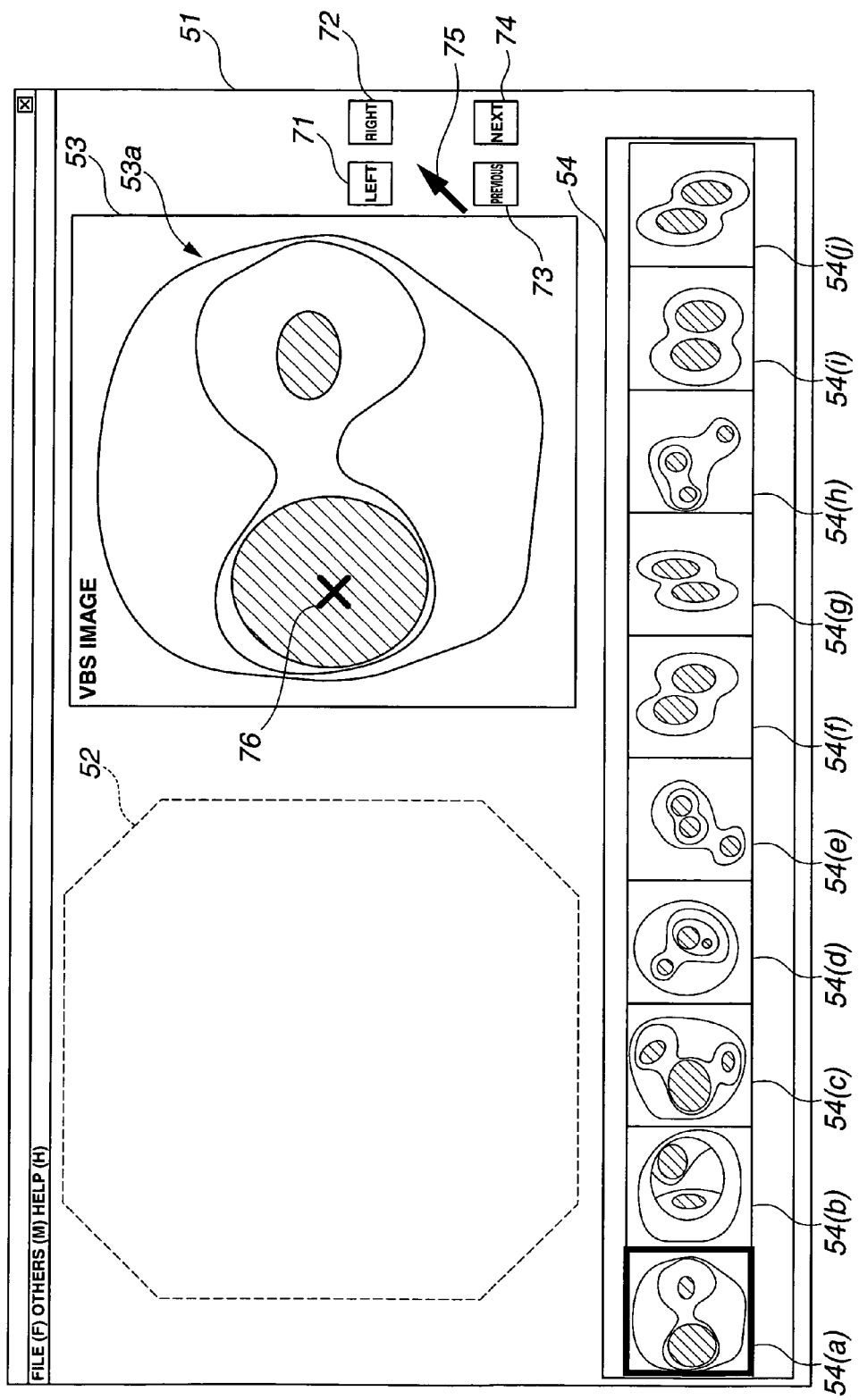
FIG. 11 is a first diagram showing an insertion support screen appearing in the processing of FIG. 10.

As illustrated in FIG. 10, when the insertion support apparatus 5 starts the simulation at Step S31, an insertion support screen 51 as shown in FIG. 11 is displayed on the monitor 7. Further, another insertion support screen 51 similar to the insertion support screen 51 displayed on the monitor 7 is also displayed on the monitor 6.

The insertion support screen 51 includes an endoscope live image display area 52 for displaying the live image obtained by the bronchoscope device 3 in the actual observation, a VBS image display area 53 for displaying a VBS image 53a, and a branch thumbnail VBS image area 54 for displaying branch thumbnail VBS images 54(a) to 54(j) which are reduced size images of the VBS image 53a at all of the branch points on the route. The VBS image 53a is displayed in the VBS image display area 53 as a virtual image corresponding to one of the branch points at which the live image is located.

One of the branch thumbnail VBS images similar to the VBS image 53a displayed in the VBS image display area 53 is framed in color or by a bold line to be distinguished from the other branch thumbnail VBS images. Accordingly, a surgeon can easily recognize which one of the branch images corresponds to the VBS image displayed in the VBS image display area 53.

Each of the branch thumbnail VBS images 54(a) to 54(j) displayed in the branch thumbnail VBS image area 54 is subjected to initialization of an image rotation angle to a predetermined value at Step S32, and thus the each of the branch thumbnail VBS images 54(a) to 54(j) is a virtual model image following the route in an initial state. In FIG. 11, an original image of the branch thumbnail VBS image 54(a) is displayed in the VBS image display area 53.

The present processing is a simulation. In FIG. 11, therefore, no image is displayed in the endoscope live image display area 52.

The insertion support screen 51 includes a left button 71, a right button 72, a previous button 73, and a next button 74. If the next button 74 is selected with the cursor 75 by using the input unit 8, the VBS image 53a can be moved forward in an insertion direction on a frame-by-frame basis. Further, if the previous button 73 is selected with the cursor 75, the VBS image 53a can be moved backward in the insertion direction on the frame-by-frame basis.

Furthermore, if the left button 71 is selected with the cursor 75, the VBS image 53a can be successively rotated in a left direction. Further, if the right button 72 is selected with the cursor 75, the VBS image 53a can be successively rotated in a right direction.

A marker 76 indicating an inserted branch hole is displayed superimposed on the VBS image 53a of each of the branch points in the bronchi. Due to reduction in diameter of the bronchoscope, the bronchoscope is generally bent only in one of up and down directions, for example. Therefore, the VBS image 53a is rotated with the left button 71 or the right button 72 such that the inserted branch hole indicated by the marker 76 is located at an upper position or a lower position in the VBS image 53a.

Figure 12:
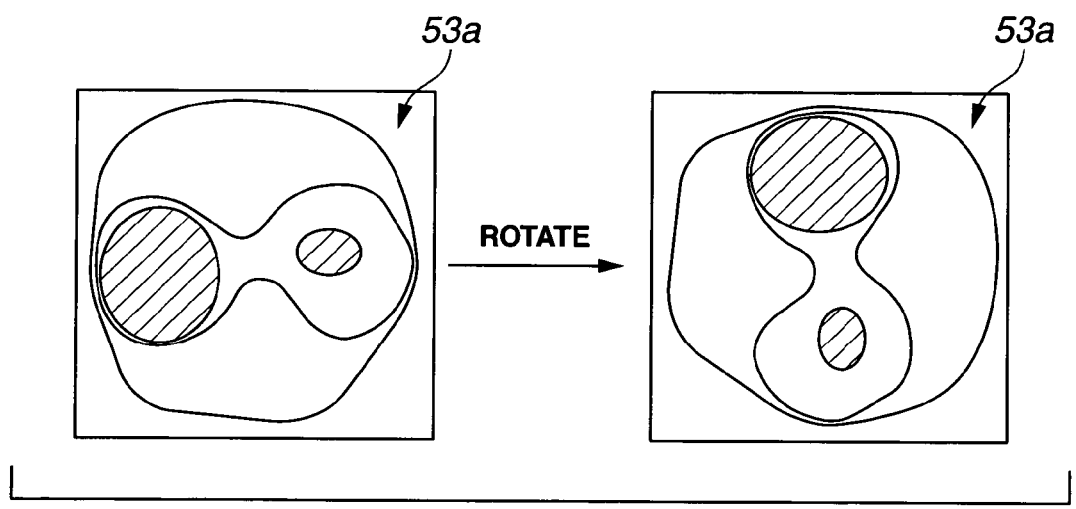
FIG. 12 is a diagram illustrating rotation of a VBS image in the insertion support screen of FIG. 11.
Figure 13:
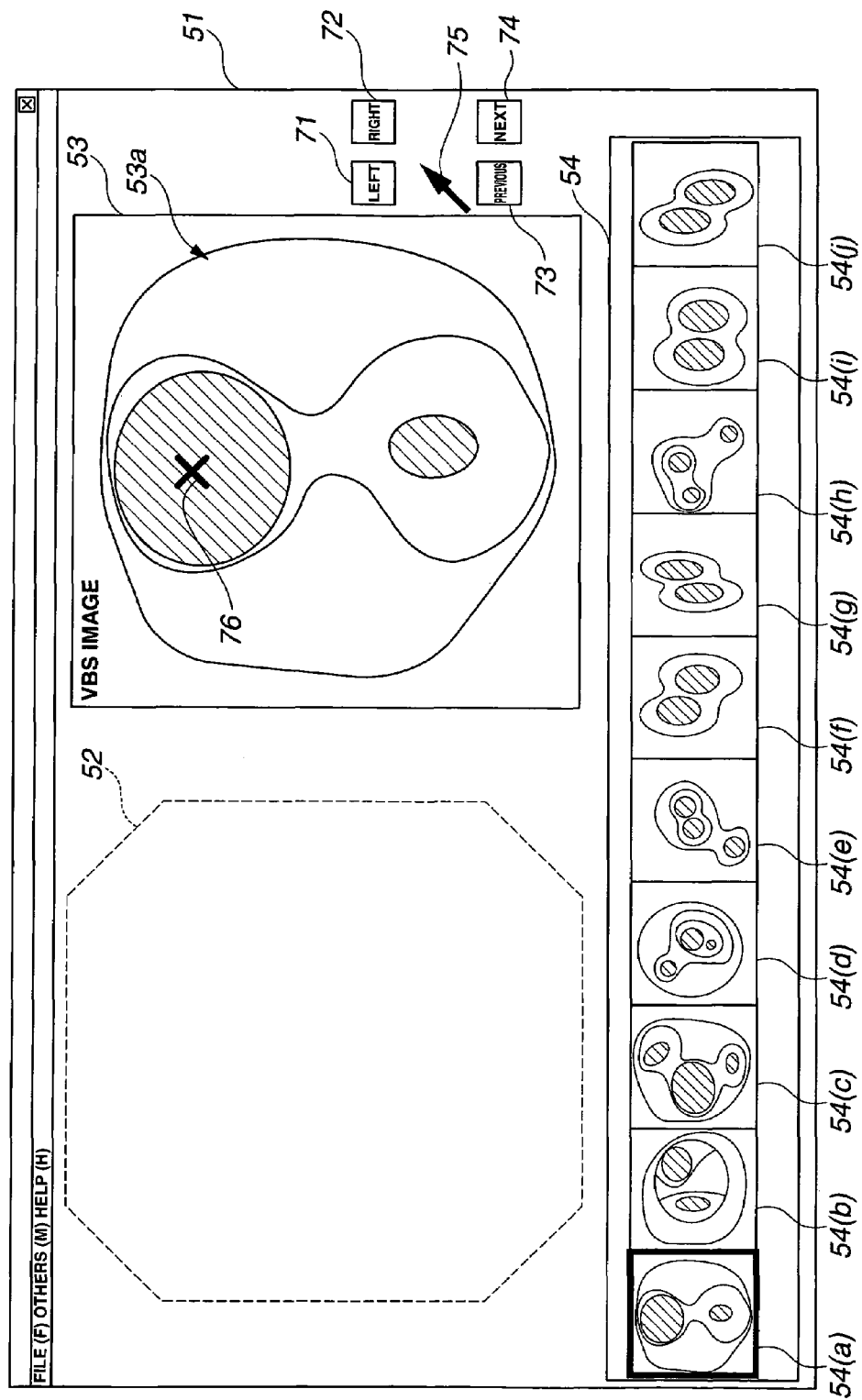
FIG. 13 is a second diagram showing the insertion support screen appearing in the processing of FIG. 10.

It is then determined at Step S33 whether the surgeon has performed a rotation operation to rotate the VBS image 53a. If it is determined that the surgeon has performed the rotation operation, it is then determined at Step S34 whether a rotation amount caused by the rotation operation is smaller than 180° with respect to the branch thumbnail VBS image 54(a). If it is determined that the rotation amount of the rotation operation is smaller than 180° with respect to the branch thumbnail VBS image 54(a), the VBS image 53a, i.e., the original image of the branch thumbnail VBS image 54(a) is rotated in accordance with the rotation operation, as illustrated in FIG. 12, for example. Then, as shown in FIG. 13, the marker 76 indicating the inserted branch hole is positioned on the VBS image 53a. Further, at Step S35, the rotation angle of the image is stored in the memory 20, with the rotation angle being linked to frame information of the VBS image 53a. Thereafter, the flow advances to Step S37. Meanwhile, if it is determined that the rotation amount of the rotation operation is equal to or larger than 180° with respect to the branch thumbnail VBS image 54(a), an error display window 79 as shown in FIG. 14 is superimposed on the insertion support screen 51 at Step S36. Thereafter, the flow advances to Step S37.

Then, it is determined whether completion of the simulation has been commanded at Step S37. If it is determined that the completion of the simulation has not been commanded, the flow returns to Step S33 to repeat necessary processings. If it is determined that the completion of the simulation has been commanded, the simulation processing is completed.

Figure 15:
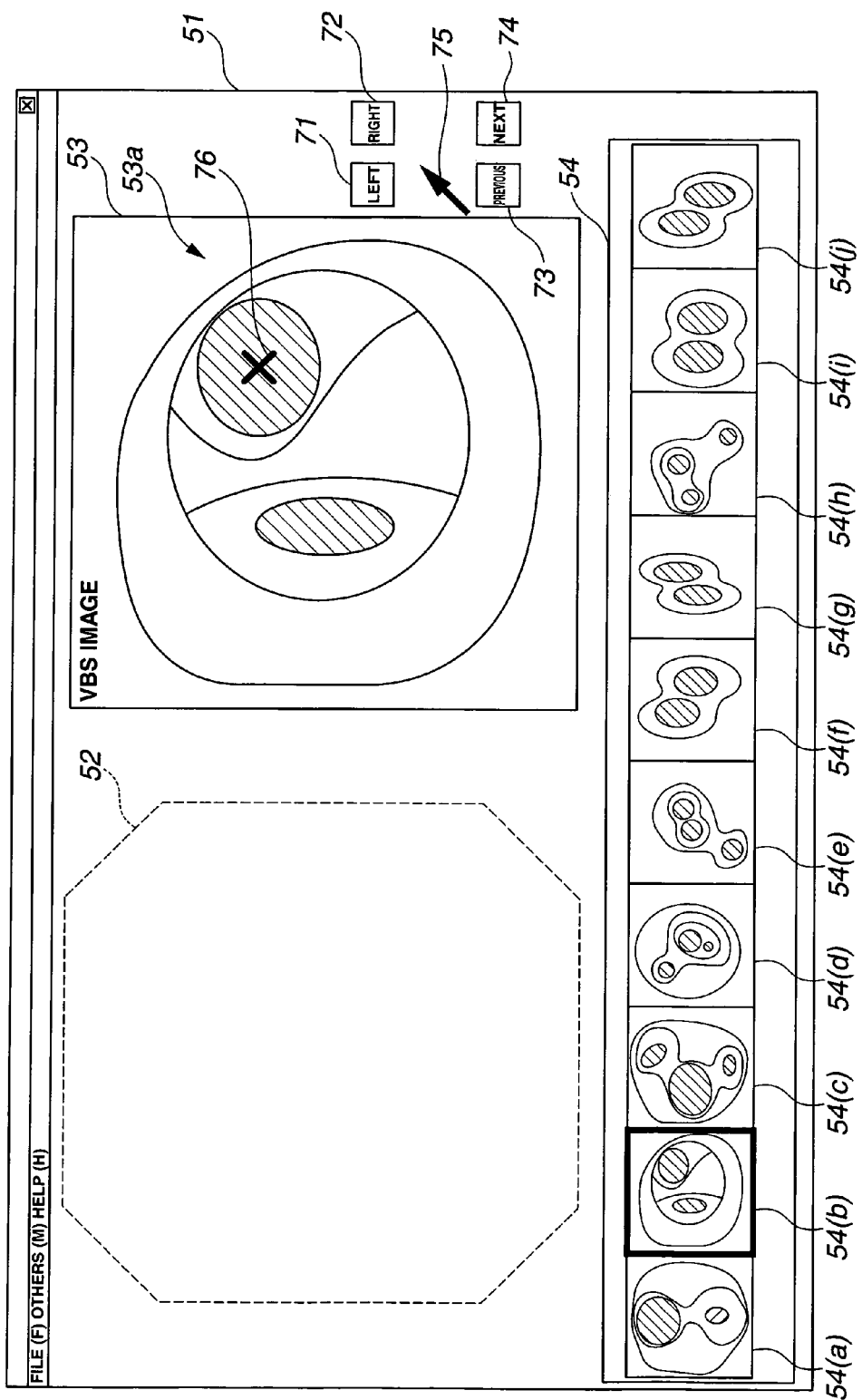
FIG. 15 is a third diagram showing the insertion support screen appearing in the processing of FIG. 10.
Figure 16:
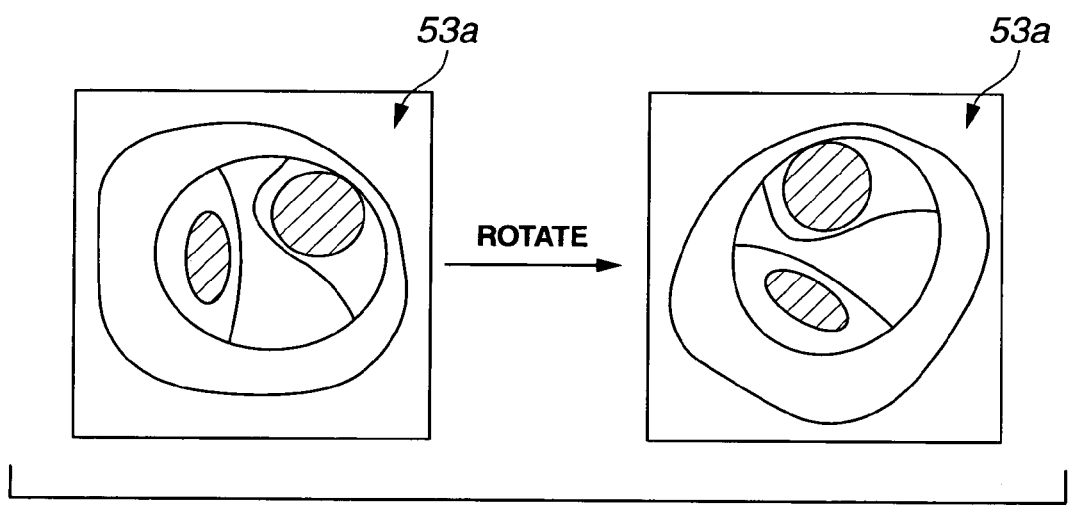
FIG. 16 is a diagram illustrating rotation of a VBS image in the insertion support screen of FIG. 15.
Figure 17:
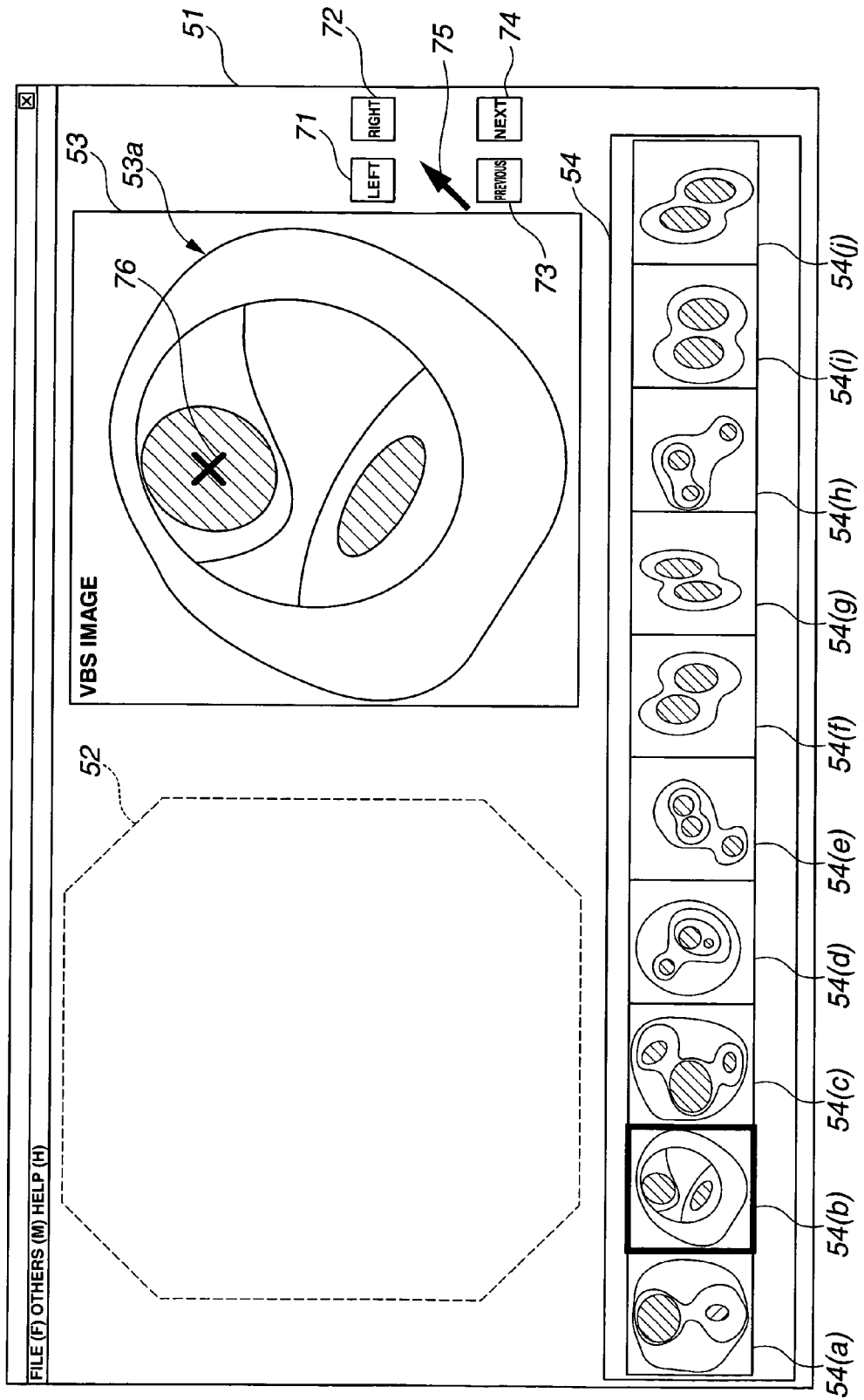
FIG. 17 is a fourth diagram showing the insertion support screen appearing in the processing of FIG. 10.

For example, if the flow returns to Step S33, and if the previous button 73 is selected with the cursor 75 to move the VBS image 53a forward to the original image of the branch thumbnail VBS image 54(b), as illustrated in FIG. 15, the branch thumbnail VBS image 54(b) is framed in color or by a bold line. This VBS image 53a, i.e., the original image of the branch thumbnail VBS image 54(b) is also rotated, as illustrated in FIG. 16. Thereby, as shown in FIG. 17, the inserted branch hole is positioned on the VBS image 53a. Further, the rotation angle of the image is stored in the memory 20, with the rotation angle being linked to frame information of the VBS image 53a.

Figure 18:
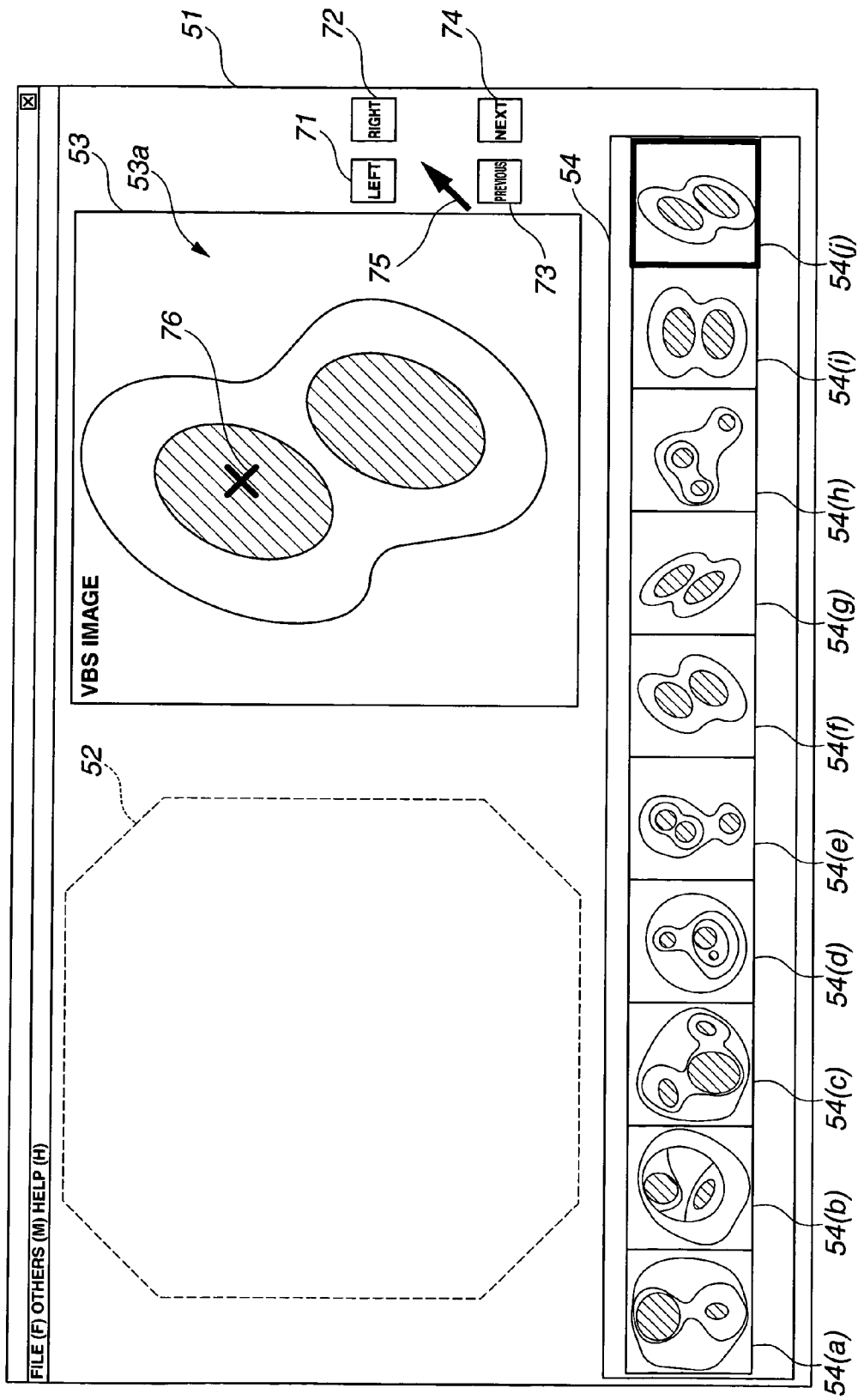
FIG. 18 is a fifth diagram showing the insertion support screen appearing in the processing of FIG. 10.

The simulation processing described above is performed for regions along the entire route. Thereby, as illustrated in FIG. 18, the branch thumbnail VBS images 54(a) to 54(j) of the respective branch points are appropriately directed for insertion of the bronchoscope.

In the memory 20, the image rotation angle is linked to the frame information for each of the frames of the VBS image 53a. Therefore, when the VBS image 53a is continuously replayed, moving images rotated in accordance with the rotation operations in the simulation can be obtained.

Figure 19:
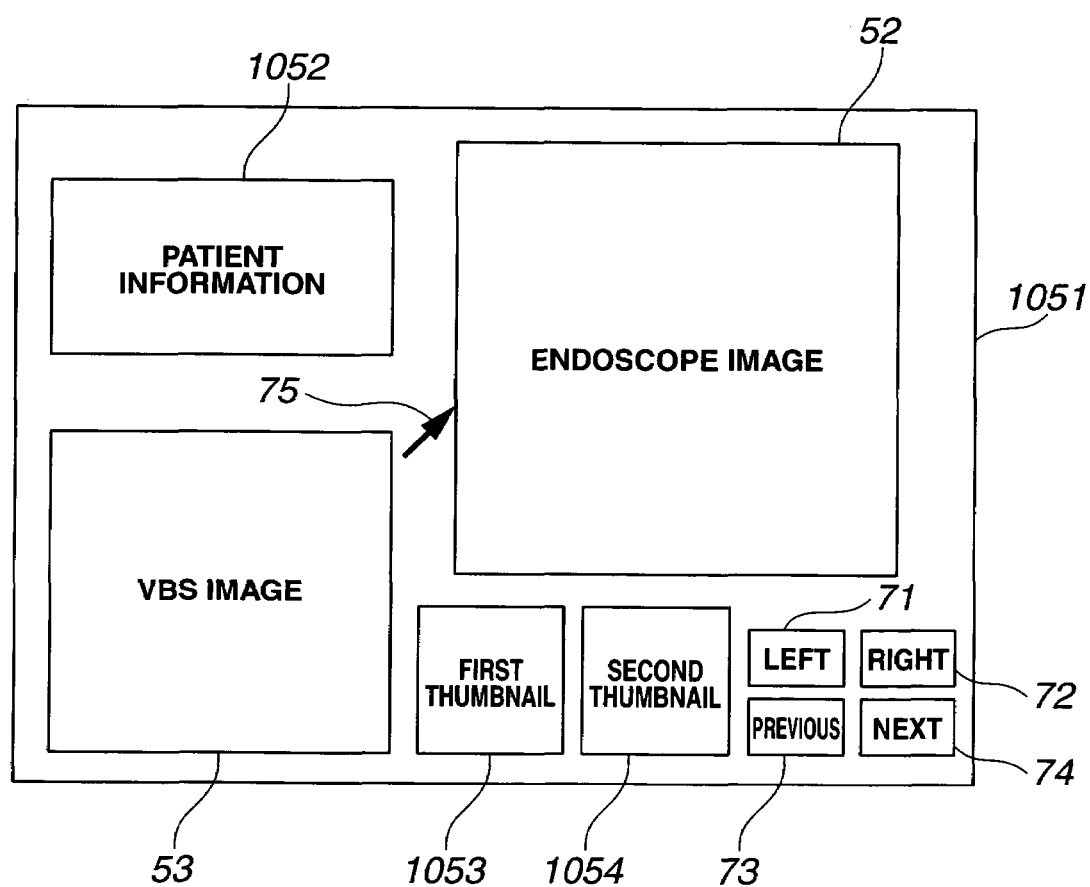
FIG. 19 is a diagram illustrating a modified example of the insertion support screen of FIG. 18.

If the monitor 7 is a display apparatus having a small display area, and if the number of the branch thumbnail VBS images displayed on the monitor 7 is increased, the branch thumbnail VBS images become unclear. Therefore, in replacement of the insertion support screen 51 shown in FIG. 18, an insertion support screen 1051 as illustrated in FIG. 19 may be displayed.

As well as the endoscope live image display area 52 and the VBS image display area 53, the insertion support screen 1051 includes a patient information display area 1052, a first branch thumbnail display area 1053, and a second branch thumbnail display area 1054. The first branch thumbnail display area 1053 and the second branch thumbnail display area 1054 display two of the branch thumbnail VBS images. For example, a pattern shown in TABLE 1 indicates an example of a display pattern of a branch thumbnail VBS image displayed in the first branch thumbnail display area 1053 and a branch thumbnail VBS image displayed in the second branch thumbnail display area 1054. In this display pattern, only the branch thumbnail preceding the displayed VBS image and the branch thumbnail following the displayed VBS image are displayed.

TABLE 1

| FIRST THUMBNAIL | SECOND THUMBNAIL |
| --- | --- |
| PREVIOUS IMAGE | NEXT IMAGE |
| NEXT IMAGE | IMAGE AFTER NEXT |
| IMAGE BEFORE PREVIOUS | PREVIOUS IMAGE |

Timing of switching display of the branch thumbnails in TABLE 1 is in conjunction with the progress of the live image and the VBS image.

If the monitor 7 has a further smaller display area, the left button 71, the right button 72, the previous button 73, and the next button 74 may be omitted from the insertion support screen 1051. In this case, button functions of the above buttons may be included in a foot switch (not illustrated).

In the following description, each of the VBS images in the frame units rotated in accordance with the rotation operation in the simulation is referred to as a rotation reflected VBS image, while each of the VBS images in the frame units having an image rotation angle initialized to a predetermined value is referred to as an initial VBS image.

Description will now be made of the support processing performed by the insertion support apparatus 5 in the actual examination in which observation and treatment are performed by using the bronchoscope, with the rotation angles being stored in the memory 20 linked to the frame information of the VBS image 53a through the insertion simulation.

Figure 20:
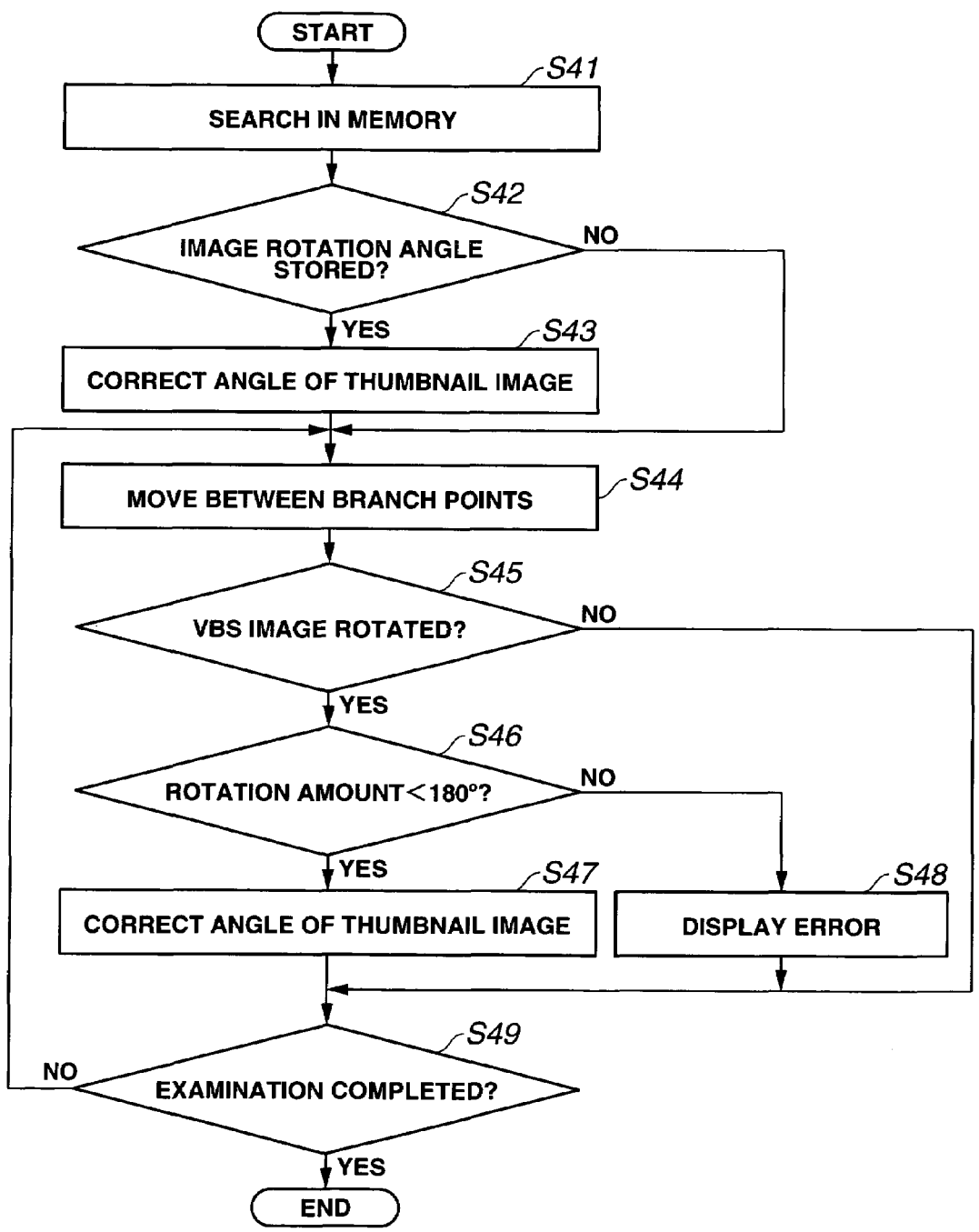
FIG. 20 is a flowchart illustrating a flow of a support processing performed by the insertion support apparatus of FIG. 1 in an examination in which observation and treatment are performed.

As illustrated in FIG. 20, when the actual examination in which observation and treatment are performed by using the bronchoscope starts, the image processing unit 17 searches in the memory 20 at Step S41. Then, it is determined at Step S42 whether the image rotation angle data linked to the frame information is stored in the memory 20. If it is determined that the image rotation angle data linked to the frame information is stored in the memory 20, angle-corrected branch thumbnail VBS images of the respective branch points are generated at Step S43 from the rotation reflected VBS image which has been rotated and corrected in accordance with the image rotation angle data, and the insertion support screen 51 is displayed on the monitor 7.

When the surgeon performs the insertion operation of the bronchoscope and the bronchoscope reaches a branch point, at Step S44, an assistant supporting the surgeon operates the cursor 75 through the input unit 8 on the insertion support screen 51 to display the VBS image of the corresponding branch point. Then, it is determined at Step S45 whether the rotation operation of the VBS image has been performed. If it is determined that the rotation operation of the VBS image has been performed, it is then determined at Step S46 whether the rotation amount caused by the rotation operation is smaller than 180° with respect to the branch thumbnail VBS image 54(a). If it is determined that the rotation amount caused by the rotation operation is smaller than 180° with respect to the branch thumbnail VBS image 54(a), the rotation angle of the branch thumbnail VBS image at the branch point is corrected and displayed in accordance with the rotation operation of the VBS image at Step S47, if the rotation operation of the VBS image has been performed. Thereafter, the flow advances to Step S49.

If it is determined at Step S45 that the rotation operation of the VBS image has not been performed, the flow directly advances to Step S49. Further, if it is determined at Step S46 that the rotation amount caused by the rotation operation is equal to or larger than 180° with respect to the branch thumbnail VBS image 54(a), the error display window 79 as shown in FIG. 14 is superimposed on the insertion support screen 51 at Step 48. Then, the flow advances to Step S49.

The Steps S44 to S49 are repeated until a command to complete the examination is received at Step 49.

If the rotation angle of the branch thumbnail VBS image is corrected at Step S47, branch thumbnail VBS images subsequent to the corrected branch thumbnail VBS image are also rotated by the same rotation angle. Thereby, the subsequent branch thumbnail VBS images are corrected and displayed. Further, VBS images of subsequent frames are also rotated by the same rotation angle and thus are corrected.

Figure 21:
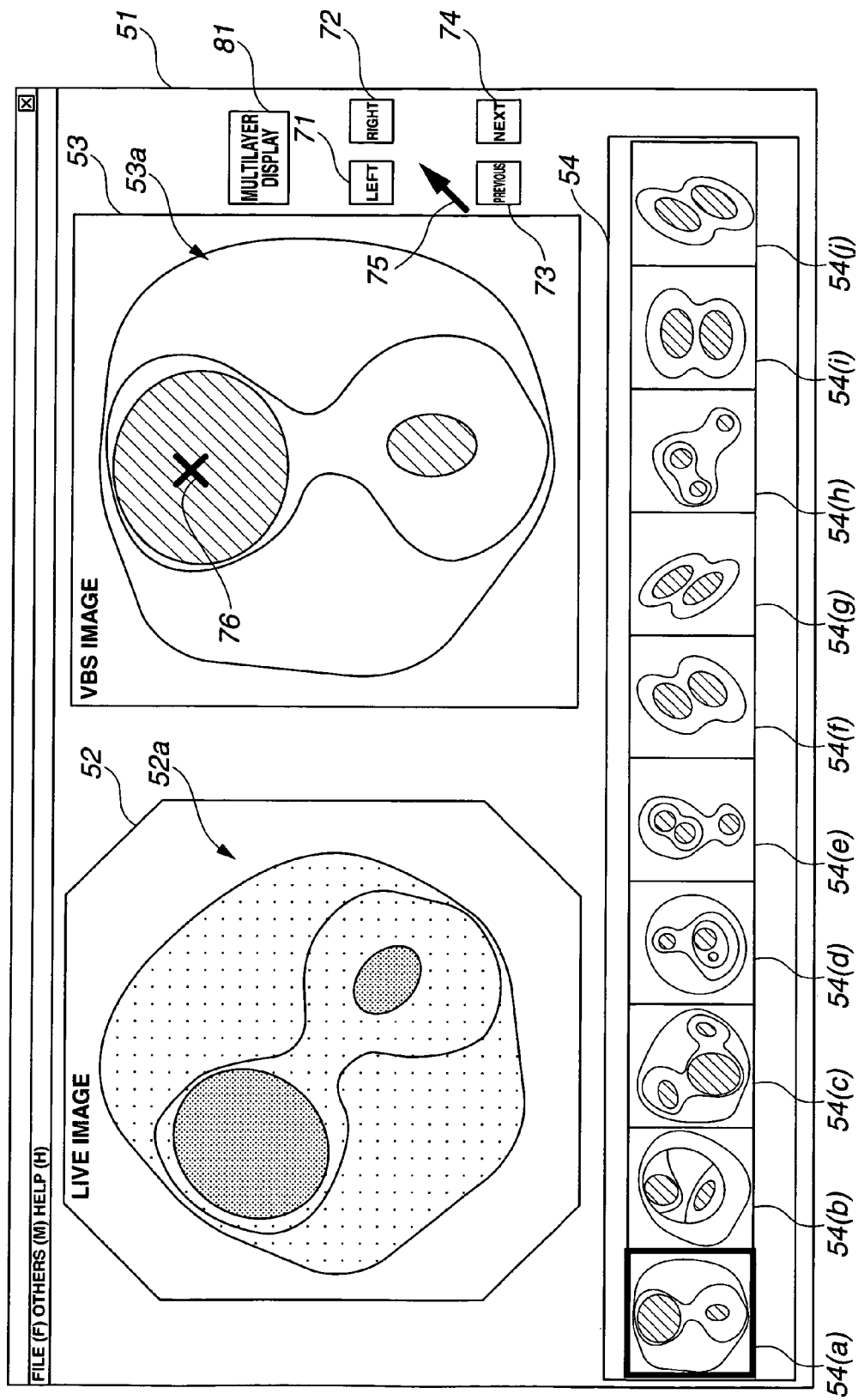
FIG. 21 is a first diagram showing the insertion support screen appearing in the processing of FIG. 20.

To be more specific on the processing of FIG. 20, if the examination starts and the memory 20 stores the image rotation angle data linked to the frame information, the insert support screen 51 as shown in FIG. 21 is displayed. The insert support screen 51 includes a multilayer display button 81, which is later described.

If the memory 20 does not store the image rotation angle data linked to the frame information, the initialized branch thumbnails as shown in FIG. 11 are displayed in the branch thumbnail VBS image area 54.

A live image 52a sent by the bronchoscope device 3 is displayed in the endoscope live image display area 52 on the insertion support screen 51 of FIG. 21. The surgeon performs a twist operation on the bronchoscope (i.e., an operation of rotating the bronchoscope around a longitudinal axis of an insert portion thereof) so that the VBS image 53a corresponds to the live image 52a of the branch point where the bronchoscope reaches. Further, the inserted branch hole is located at an upper position or a lower position on the live image 52a.

Figure 22:
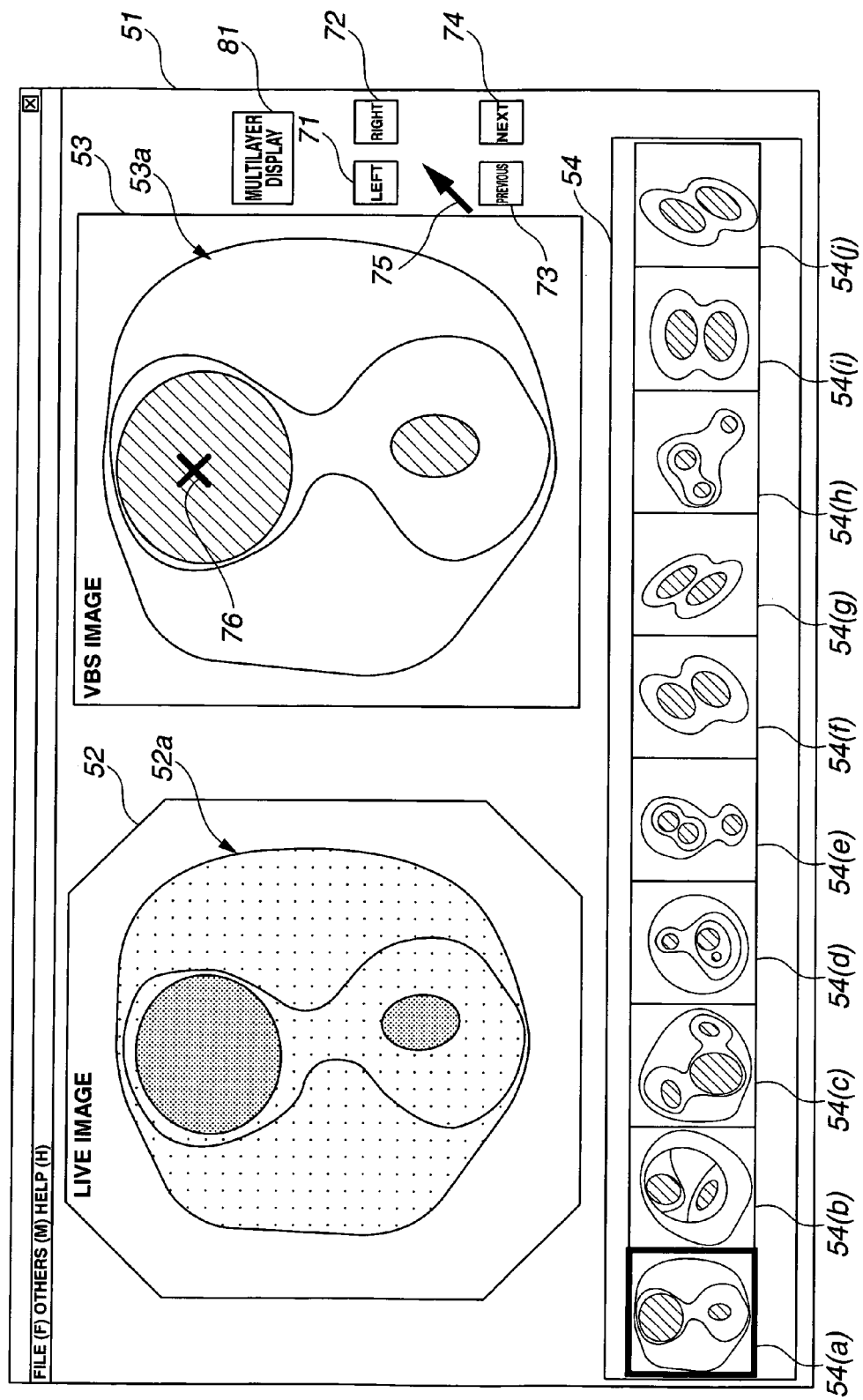
FIG. 22 is a second diagram showing the insertion support screen appearing in the processing of FIG. 20.

FIG. 21 shows the insertion support screen 51 displaying the rotation reflected VBS image 53a of a first branch point shown by the branch thumbnail VBS image 54(a). FIG. 22 shows the insertion support screen 51 displaying the live image 52a on which the inserted branch hole is positioned after having performed the twist operation on the bronchoscope in accordance with the VBS image 53a of FIG. 21.

Then, the distal end of the insert portion of the bronchoscope is guided into the inserted branch hole, and the insertion of the bronchoscope continues.

Figure 23:
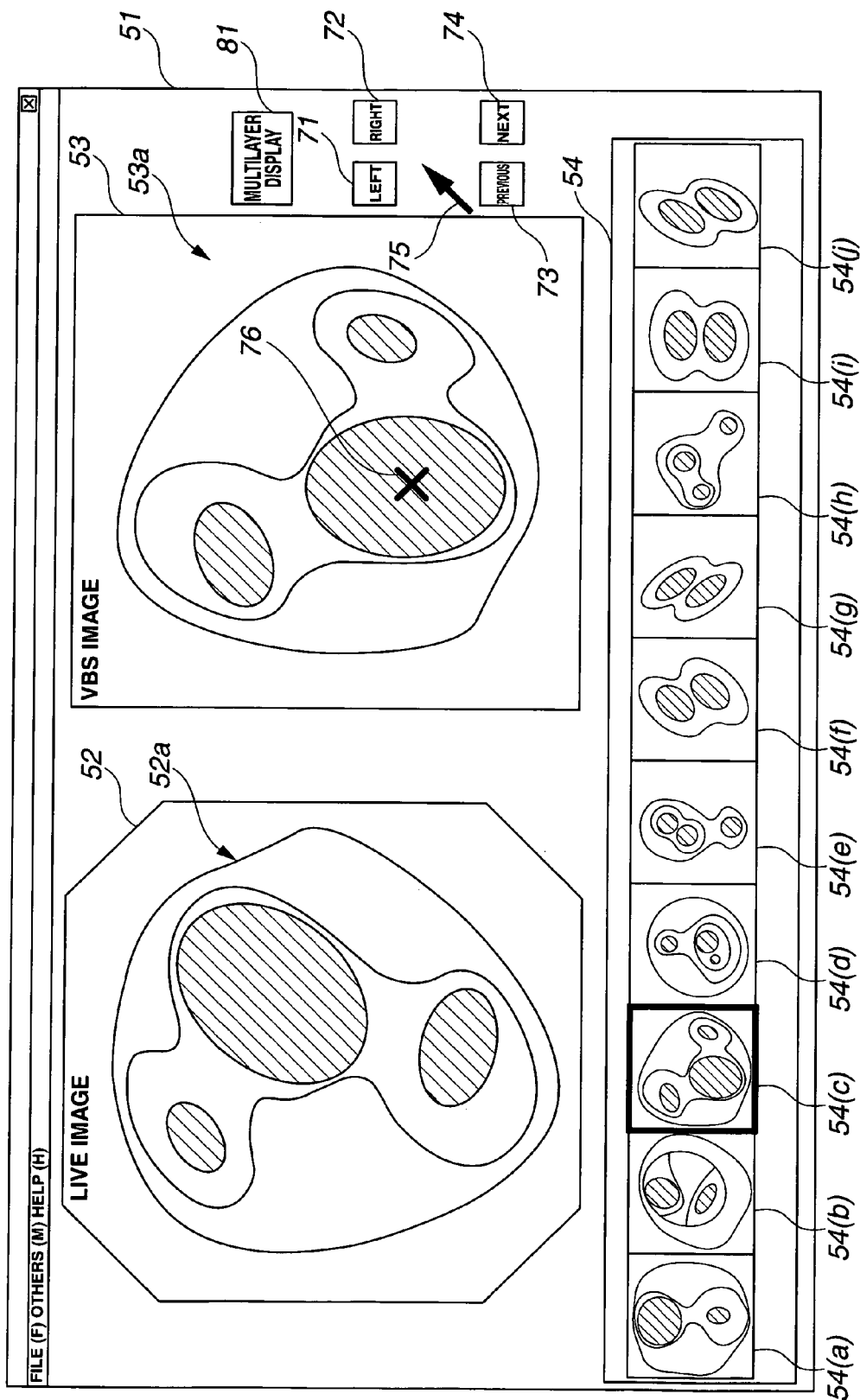
FIG. 23 is a third diagram showing the insertion support screen appearing in the processing of FIG. 20.

FIG. 23 shows the insertion support screen 51 displaying the rotation reflected VBS image 53a of a third branch point shown by the branch thumbnail VBS image 54(c).

The live image 52a is constantly applied with irregular rotations due to the twist operation of the bronchoscope performed when inserting the bronchoscope into the route. Therefore, for example, if the inserted branch hole is located at a lower position in the VBS image 53a, as illustrated in FIG. 23, the live image 52a does not correspond to the rotation reflected VBS image 53a in some cases, unless the twist operation is performed with a large twist amount. Therefore, prior to the twist operation of the bronchoscope, the rotation reflected VBS image 53a is rotated to reduce the twist amount.

Figure 24:
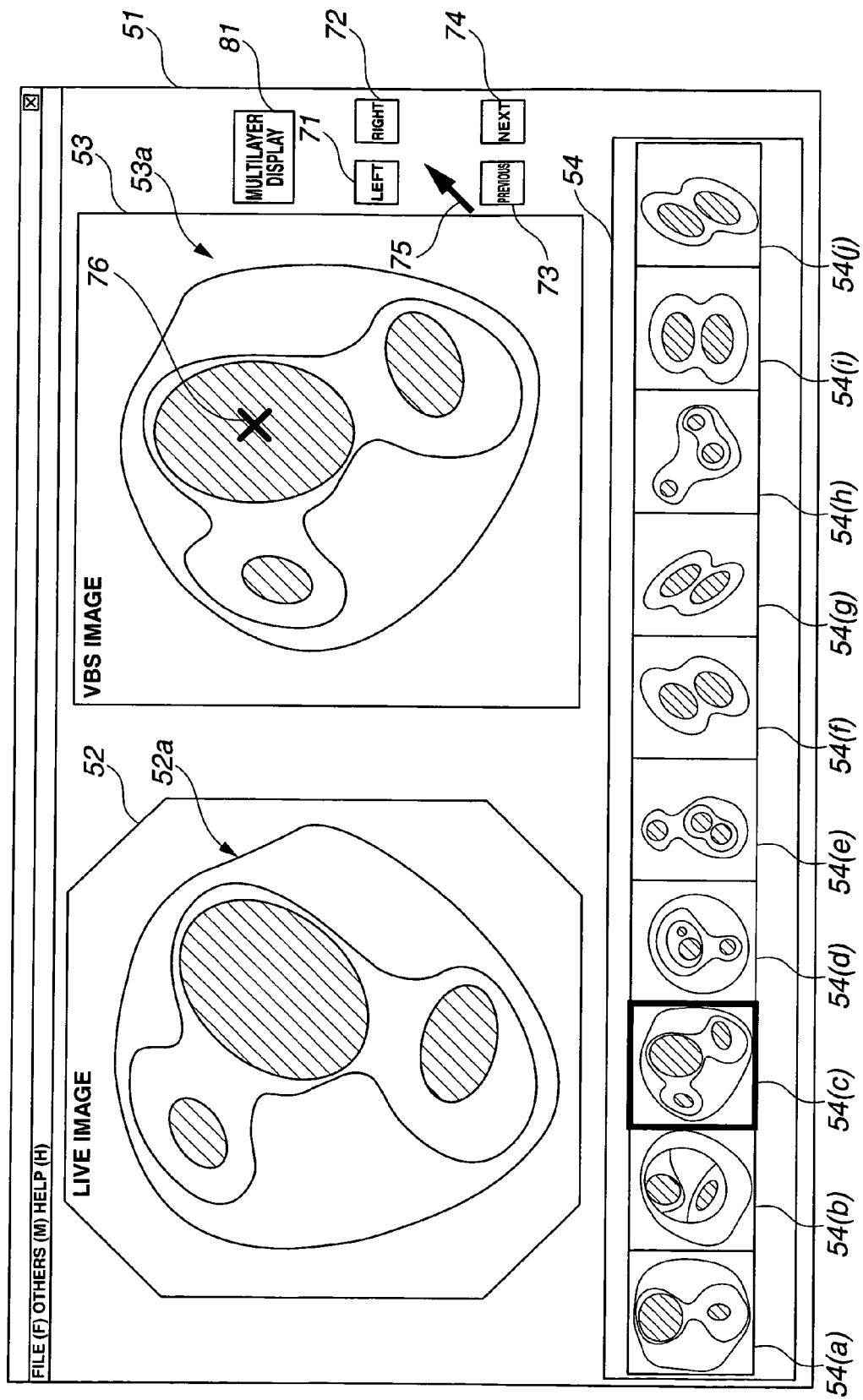
FIG. 24 is a fourth diagram showing the insertion support screen appearing in the processing of FIG. 20.
Figure 25:
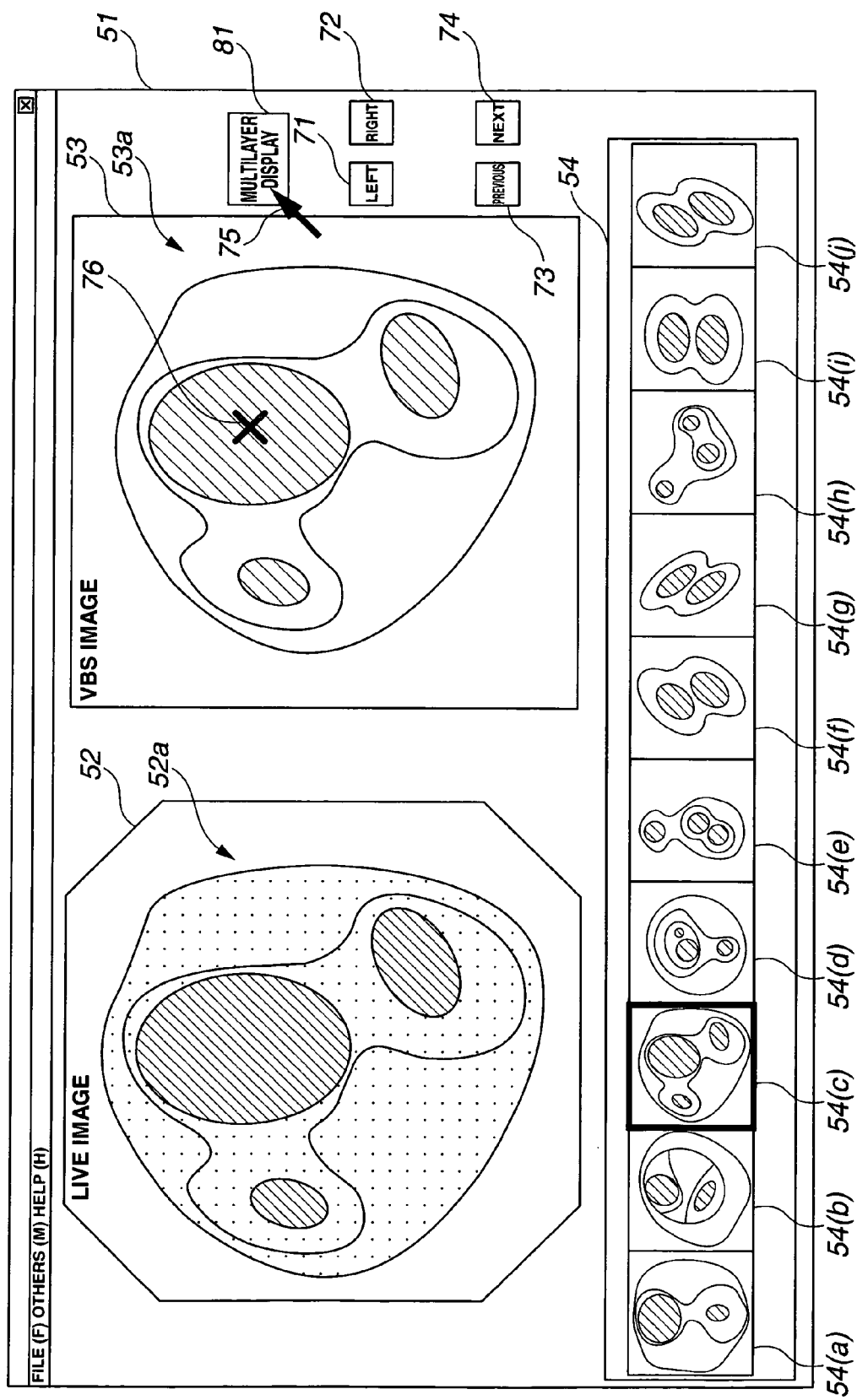
FIG. 25 is a fifth diagram showing the insertion support screen appearing in the processing of FIG. 20.

FIG. 24 shows the insertion support screen 51 displaying the VBS image 53a on which the inserted branch hole is positioned after having rotated the rotation reflected VBS image 53a of FIG. 23. FIG. 25 shows the insertion support screen 51 displaying the live image 52a on which the inserted branch hole is positioned after having performed the twist operation on the bronchoscope in accordance with the VBS image 53a of FIG. 24.

Figure 26:
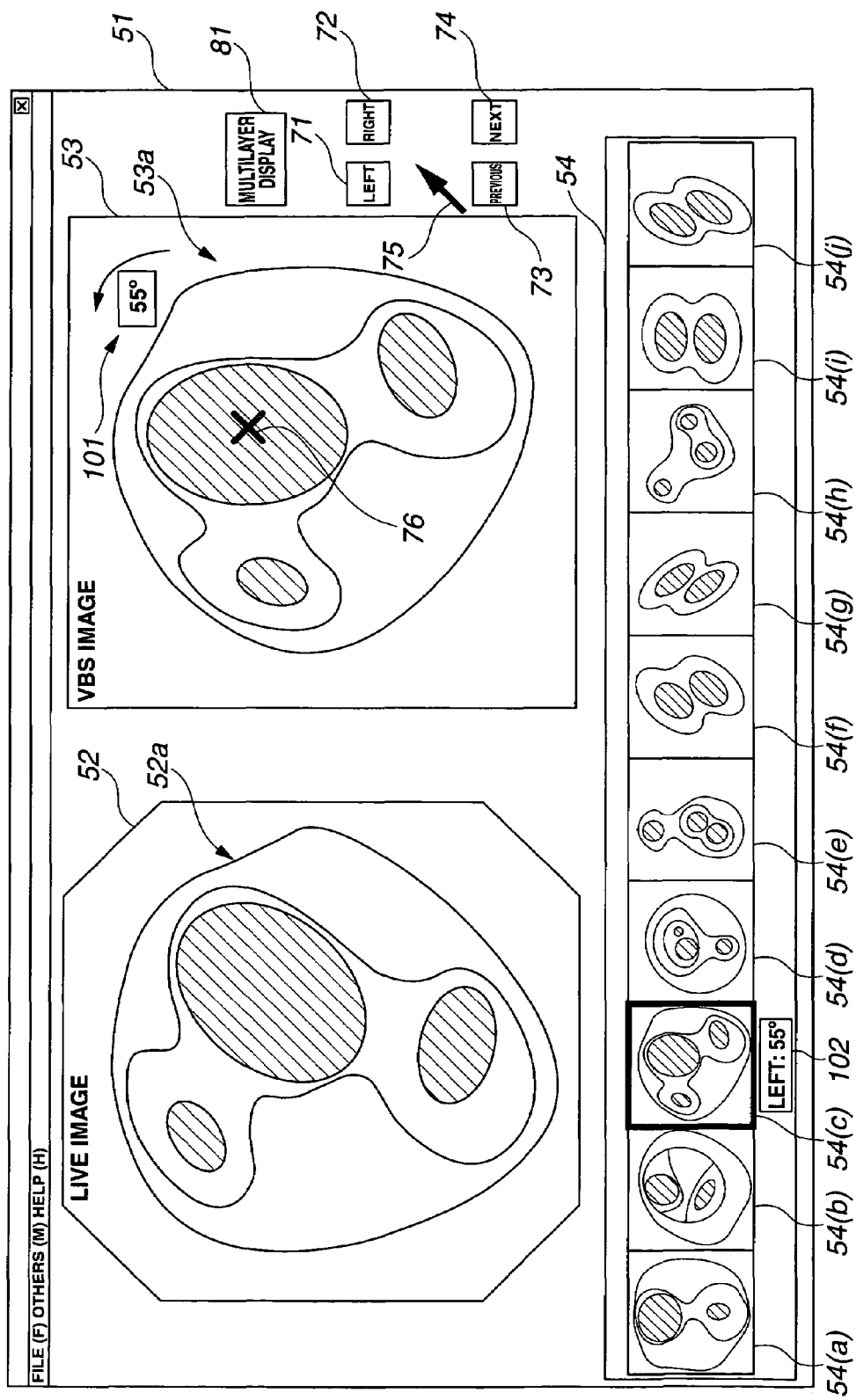
FIG. 26 is a first diagram illustrating a modified example of the insertion support screen of FIG. 24.
Figure 27:
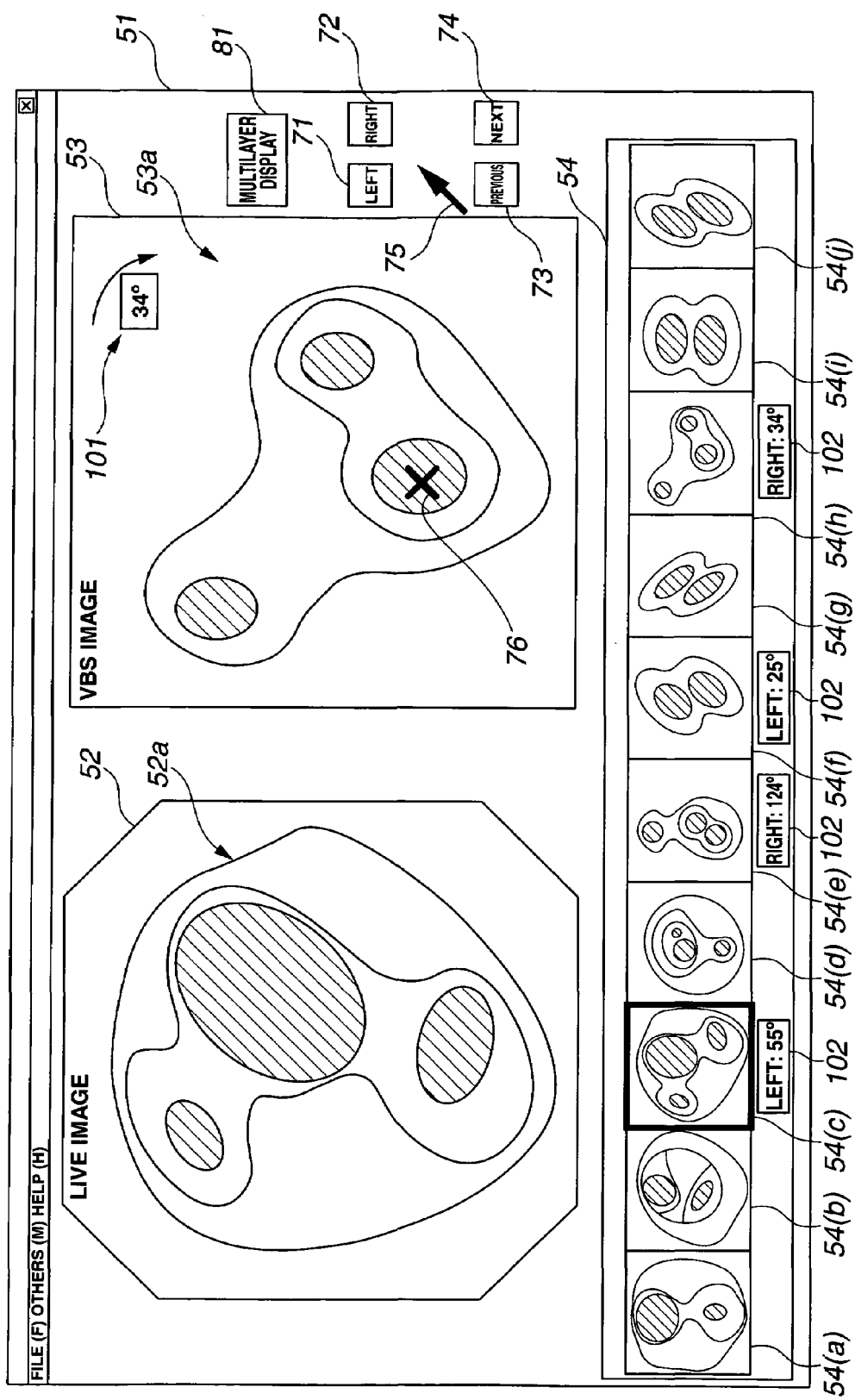
FIG. 27 is a second diagram illustrating a modified example of the insertion support screen of FIG. 24.

As illustrated in FIG. 26, in the rotation reflected VBS image 53a shown in FIG. 24, the rotation amount with respect to the branch thumbnail VBS image 54(a) of the first branch point is read from the memory 20. Thus, rotation information 101 including a rotation direction and the rotation amount can be superimposed on the rotation reflected VBS image 53a. Further, rotation information 102 can be displayed under the branch thumbnail VBS image 54(c). In this case, as illustrated in FIG. 27, the rotation information 102 with respect to the branch thumbnail VBS image 54(a) may be displayed under all of the rotated branch thumbnail VBS images. Accordingly, the process of the twist operation of the bronchoscope can be easily understood.

If the multilayer display button 81 on the insertion support screen 51 is selected with the cursor 75, pattern diagrams of the inserted branch hole at branch points subsequent to a current branch point are displayed in multi-layers on the inserted branch hole shown on the VBS image 53a of the current branch point, as described below.

Figure 28:
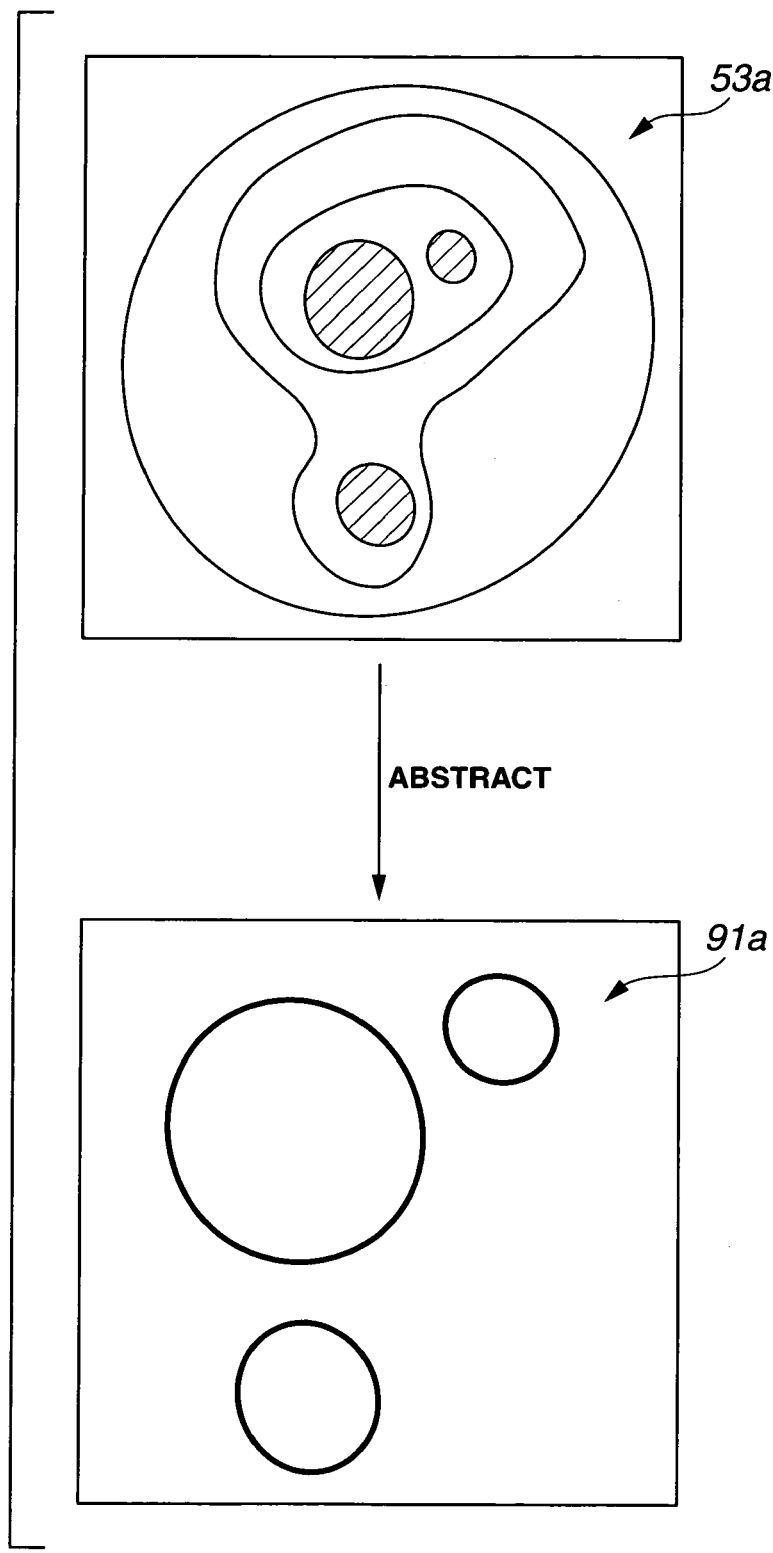
FIG. 28 is a first diagram illustrating the processing performed when the multilayer display button on the insertion support screen of FIG. 25 is selected.
Figure 29:
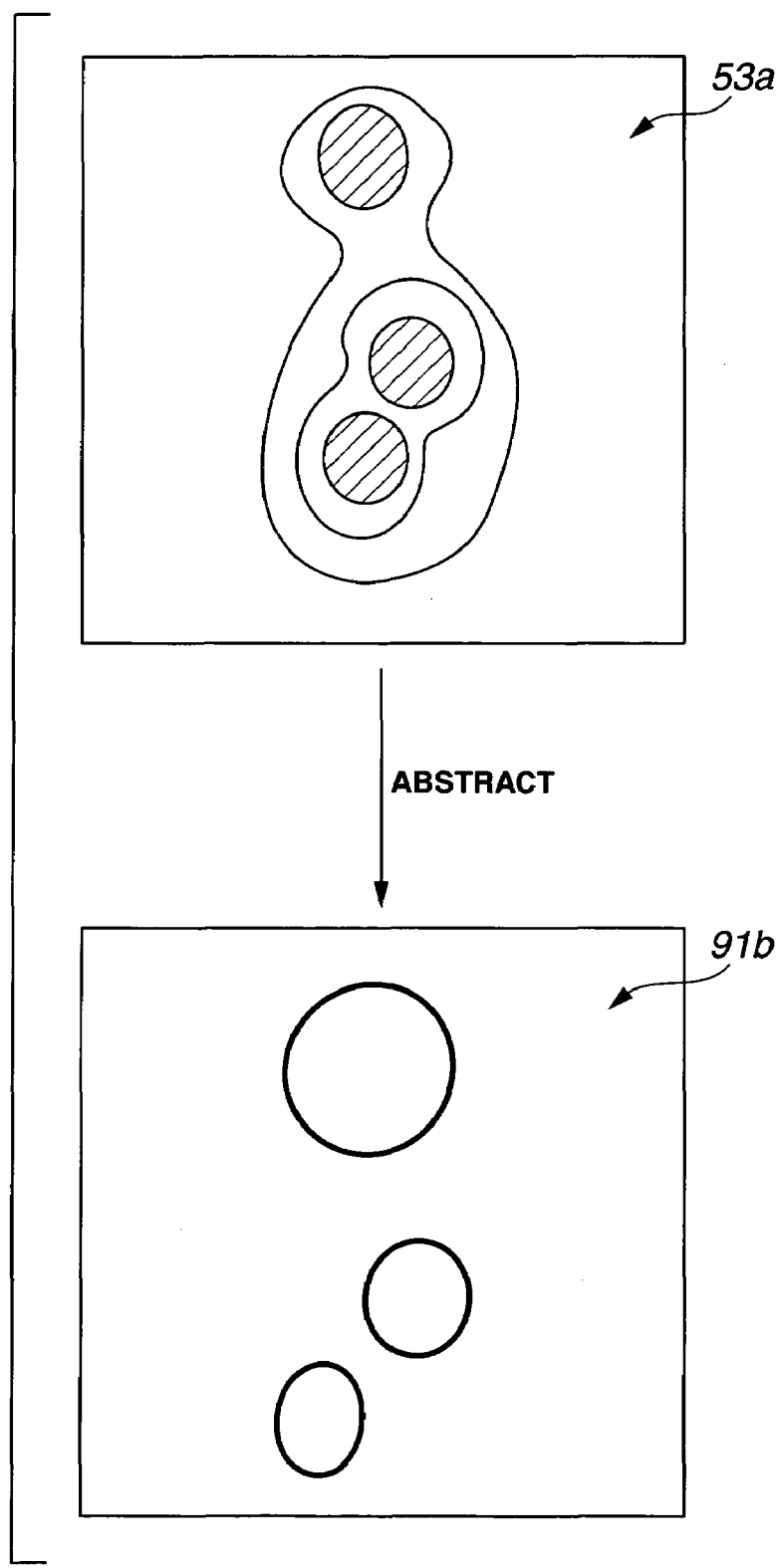
FIG. 29 is a second diagram illustrating the processing performed when the multilayer display button on the insertion support screen of FIG. 25 is selected.

That is, if the multilayer display button 81 is selected on the insertion support screen 51 of FIG. 25 which displays the rotation reflected VBS image 53a of the third branch point shown by the branch thumbnail VBS image 54(c), for example, (1) as illustrated in FIG. 28, an outline of the inserted branch hole on the rotation reflected VBS image 53a of a fourth branch point shown by the branch thumbnail VBS image 54(d) is extracted and abstracted to generate a pattern diagram 91a. Further, (2) as illustrated in FIG. 29, an outline of the inserted branch hole on the rotation reflected VBS image 53a of a fifth branch point shown by the branch thumbnail VBS image 54(e) is extracted and abstracted to generate a pattern diagram 91b.

Figure 30:
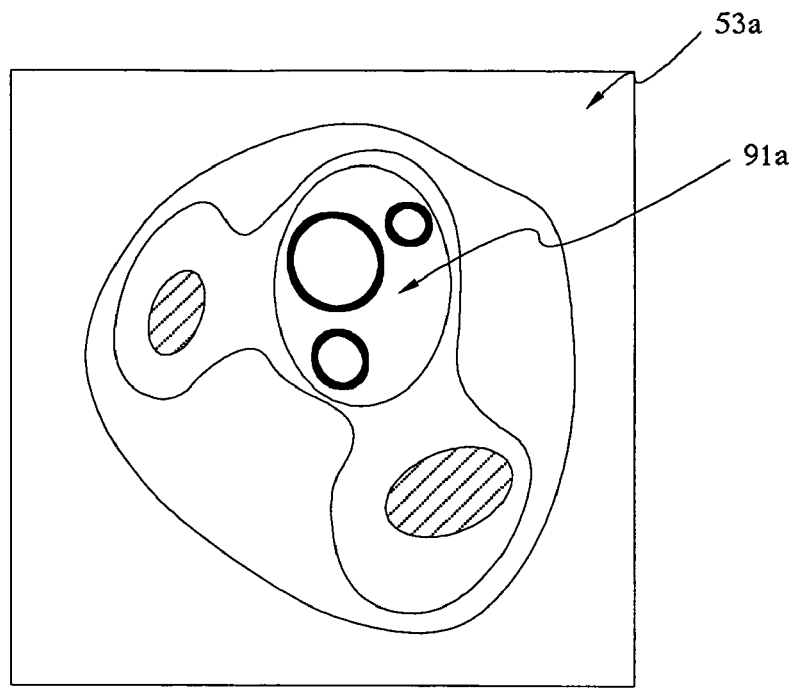
FIG. 30 is a third diagram illustrating the processing performed when the multilayer display button on the insertion support screen of FIG. 25 is selected.
Figure 31:
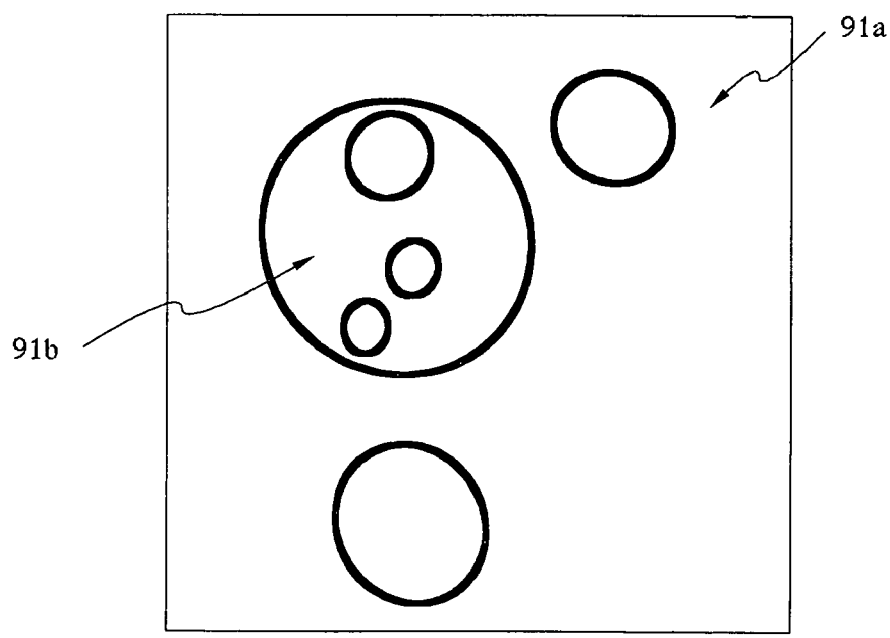
FIG. 31 is a fourth diagram illustrating the processing performed when the multilayer display button on the insertion support screen of FIG. 25 is selected.
Figure 32:
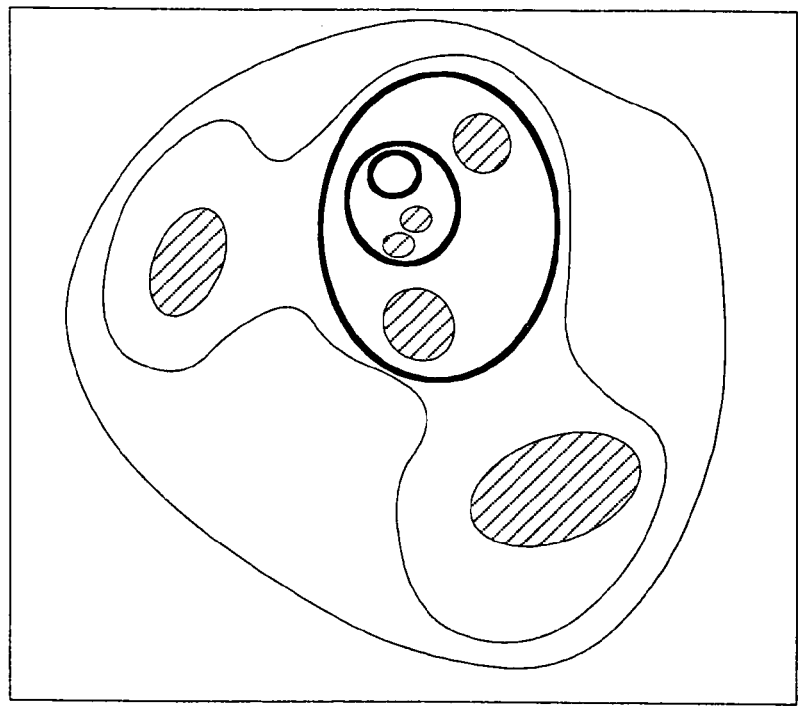
FIG. 32 is a fifth diagram illustrating the processing performed when the multilayer display button on the insertion support screen of FIG. 25 is selected.

Then, (3) as illustrated in FIG. 30, the pattern diagram 91a of the fourth branch is reduced in size to fit in the inserted branch hole on the rotation reflected VBS image 53a of the third branch point. Similarly, (4) as illustrated in FIG. 31, the pattern diagram 91b of the fifth branch point is reduced in size to fit in the inserted branch hole on the pattern diagram 91a of the fourth branch point. Then, (5) as illustrated in FIG. 32, the pattern diagram 91a of the fourth branch point, which has the inserted branch hole including the pattern diagram 91b of the fifth branch point, is superimposed on the inserted branch hole on the rotation reflected VBS image 53a of the third branch point. Thereby, the insertion support screen 51 including the rotation reflected VBS image 53a on which the branch holes are displayed in multi-layers is generated.

Figure 33:
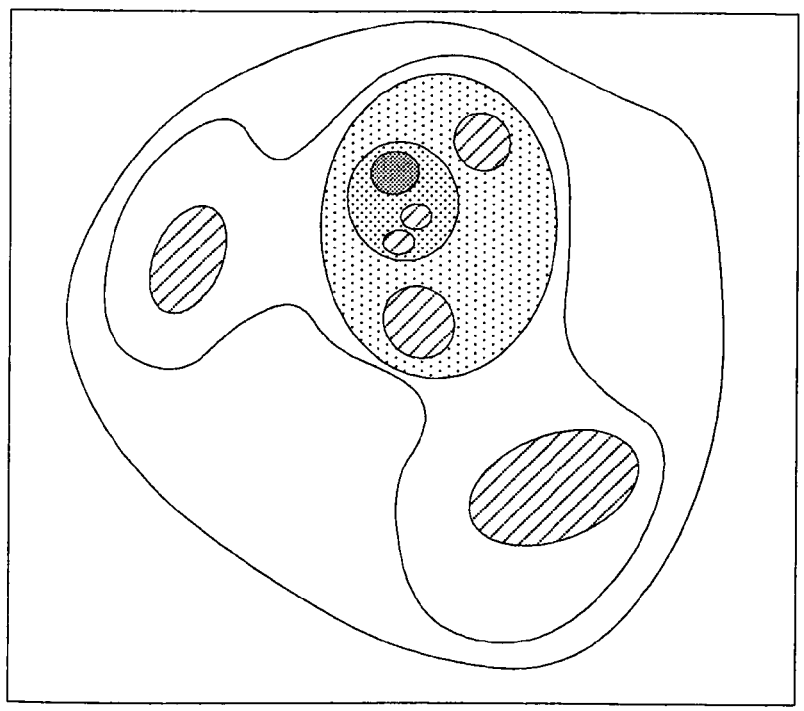
FIG. 33 is a sixth diagram illustrating the processing performed when the multilayer display button on the insertion support screen of FIG. 25 is selected.

In FIG. 32, the branch holes displayed in multi-layers on the rotation reflected VBS image 53a are indicated by bold lines. Alternatively, the multi-layers may be marked by separate colors, as illustrated in FIG. 33. Further, the number of layers forming the multi-layers is not limited to three.

As described above, in the present embodiment, the image rotation angle data is stored in the memory 20 linked to the frame information through the simulation performed prior to the actual operation. Then, on the basis of the image rotation angle data thus stored, the VBS image and the thumbnail VBS images are rotated and corrected, and the insertion support screen is generated and displayed for the insertion support. Thus, the virtual endoscope images at a plurality of branch points in the bronchi are obtained in accordance with the insert operation of the bronchoscope into the bronchi. Accordingly, the present embodiment can effectively support the insertion of the bronchoscope into the bronchi.

Conventional techniques only provide information of a current branch point as support information, and thus information of the state of a next branch point is not sufficiently obtained. Meanwhile, according to the present embodiment, the inserted branch hole is displayed in multi-layers. Therefore, the information of the state of the next branch point is easily obtained, and thus the insertion of the bronchoscope can be effectively supported.

The present invention is not limited to the embodiment described above, but can be modified or altered in various ways within a scope not changing the gist of the present invention.

What is claimed is:

1. An insertion support system comprising:
   virtual image generating unit for generating three-dimensional images of a duct in a body cavity in a subject as successive virtual images in frame units, on the basis of image data of a three-dimensional region in the subject;
   navigation image generating unit for generating a navigation image including an endoscope configured to capture images of the duct in the body cavity in subject, the virtual image, and a plurality of reduced size images of the virtual image at all branch points at which the duct in the body cavity in the subject diverges;
   rotation information storing unit for storing image rotation information of the reduced size images;
   rotation amount comparing unit for comparing the image rotation information of the reduced size images and rotation angle data of the virtual image; and
   image rotation controlling unit for rotating the reduced size images generated by the navigation image generating unit, on the basis of a result of the comparison made by the rotation amount comparing unit.

2. The insertion support system according to claim 1, wherein the rotation information storing unit stores the image rotation information in association with frame information of the virtual images.

3. The insertion support system according to claim 1, further comprising means which reads, from the rotation information storing unit, a rotation amount with respect to a virtual image at a first branch point at which the duct in the body cavity in the subject diverges, and displays information on the rotation amount together with an image rotated by the image rotation controlling unit.

4. The insertion support system according to claim 1, further comprising means which displays in multi-layers, on a pattern diagram generated by extracting and abstracting an outline of an inserted branch hole on a virtual image of a current branch point, pattern diagrams generated by extracting and abstracting an outline of an inserted branch hole at branch points subsequent to the current branch point.

* * * * *